US012213881B2

(12) United States Patent
Havel et al.

(10) Patent No.: US 12,213,881 B2
(45) Date of Patent: Feb. 4, 2025

(54) SYSTEMS AND METHODS FOR APPLYING PRESSURE TO A BODILY ORGAN

(71) Applicant: Muffin Incorporated, West Lafayette, IN (US)

(72) Inventors: William J. Havel, West Lafayette, IN (US); Neal E. Fearnot, West Lafayette, IN (US); Jeremy T. Newkirk, West Lafayette, IN (US); Shaun Davis Gittard, Winston-Salem, NC (US); John C. Sigmon, Jr., Winston-Salem, NC (US); Gregory James Hardy, Asheville, NC (US); Rita Hadley, Otterbein, IN (US); Yun Zhou, Eden Prairie, MN (US); Mitch Turley, West Lafayette, IN (US); David Reuter, Bellevue, WA (US)

(73) Assignee: Muffin Incorporated, West Lafayette, IN (US)

( * ) Notice: Subject to any disclaimer, the term of this patent is extended or adjusted under 35 U.S.C. 154(b) by 330 days.

(21) Appl. No.: 17/032,283

(22) Filed: Sep. 25, 2020

(65) Prior Publication Data

US 2021/0093452 A1     Apr. 1, 2021

Related U.S. Application Data

(60) Provisional application No. 62/906,399, filed on Sep. 26, 2019.

(51) Int. Cl.
*A61F 2/24* (2006.01)
*A61F 2/48* (2006.01)

(52) U.S. Cl.
CPC .......... *A61F 2/2445* (2013.01); *A61F 2/482* (2021.08); *A61F 2210/0014* (2013.01);
(Continued)

(58) Field of Classification Search
CPC .... A61F 2/2478; A61F 2/2481; A61F 2/2445; A61B 5/6831; A61B 17/0487
See application file for complete search history.

(56) References Cited

U.S. PATENT DOCUMENTS 9,656,009 B2 * 5/2017 Kheradvar .......... A61M 60/462
9,987,135 B2 * 6/2018 Lederman ............ A61F 2/2481
(Continued)

FOREIGN PATENT DOCUMENTS

WO    WO 2000/69323      11/2000
WO    WO 2001/91667 A2   12/2001
(Continued)

*Primary Examiner* — Brian A Dukert
(74) *Attorney, Agent, or Firm* — Woodard Emhardt Henry Reeves & Wagner

(57) ABSTRACT

Among other things, there are disclosed embodiments of belts or bands that can be used in treatments for tricuspid valve regurgitation. In some embodiments, such belts may be heat-set in a particular configuration to effectively decrease tricuspid annulus when deployed around the atrioventricular groove. Embodiments include one or more tensioning sutures for applying cinching or tightening to belts when deployed, and structure for effectively distributing force during such tightening. Embodiments of tensioning members, protective members, and devices and methods for open-surgical placement (e.g. around a heart for annuloplasty) are also disclosed.

11 Claims, 15 Drawing Sheets

(52) U.S. Cl.
CPC .............. *A61F 2210/0019* (2013.01); *A61F 2220/0075* (2013.01); *A61F 2230/0008* (2013.01); *A61F 2230/0095* (2013.01); *A61F 2250/0096* (2013.01)

(56) References Cited

U.S. PATENT DOCUMENTS

| | | |
|---|---|---|
| 10,463,495 B2 * | 11/2019 | Rogers ................. A61B 17/221 |
| 2004/0064014 A1 | 4/2004 | Melvin et al. |
| 2005/0059931 A1 | 3/2005 | Garrison et al. |
| 2008/0312493 A1 * | 12/2008 | Mortier ............ A61B 17/00234 600/37 |
| 2011/0319917 A1 | 12/2011 | Ferrera et al. |
| 2016/0038237 A1 | 2/2016 | Lederman et al. |
| 2016/0120647 A1 | 5/2016 | Rogers et al. |
| 2018/0049731 A1 | 2/2018 | Hardy et al. |
| 2018/0098850 A1 | 4/2018 | Rafiee et al. |

FOREIGN PATENT DOCUMENTS

| | | |
|---|---|---|
| WO | WO 2003/022131 A2 | 3/2003 |
| WO | WO 2004/052594 A2 | 6/2004 |
| WO | WO 2004/093730 A2 | 11/2004 |
| WO | WO 2019/089754 A1 | 5/2019 |

* cited by examiner

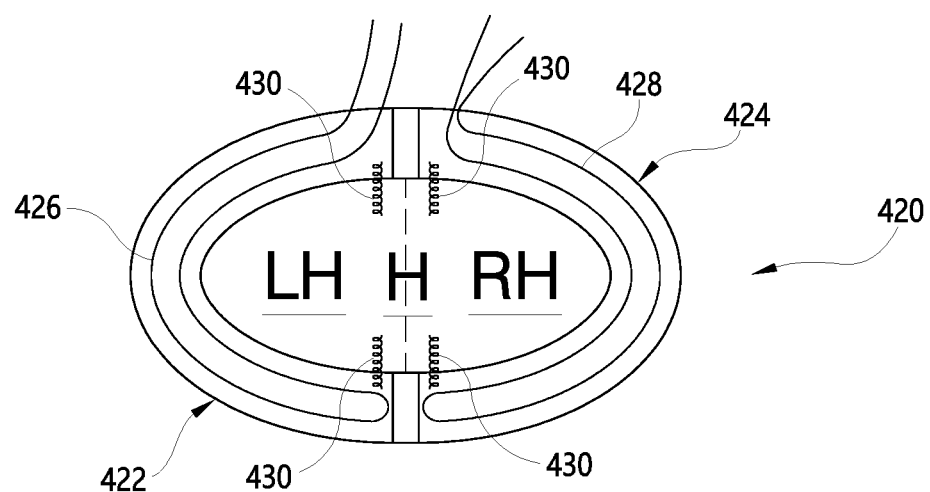
*Fig. 18*
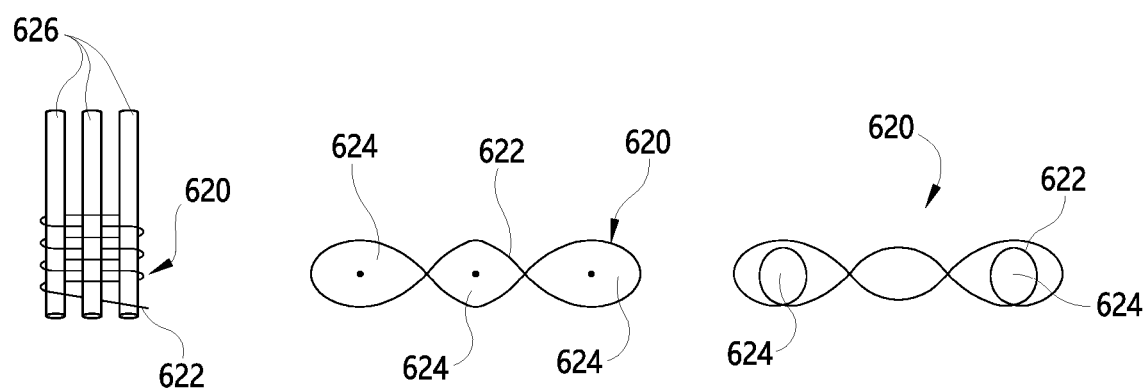
*Fig. 20A*  *Fig. 20B*  *Fig. 20C*

SYSTEMS AND METHODS FOR APPLYING PRESSURE TO A BODILY ORGAN

REFERENCE TO RELATED APPLICATION

This application claims the benefit of U.S. Provisional Patent Application Ser. No. 62/906,399, filed Sep. 26, 2019, which is hereby incorporated herein by reference in its entirety.

The current disclosure generally concerns devices for insertion into a patient's body to apply compression to an organ as a way of treating a condition of the patient. In particular, embodiments of a belt for application at least partially around an organ are disclosed.

BACKGROUND

In the treatment of tricuspid valve regurgitation (TR), it has been proposed to deliver a belt or band around the heart, and particularly into the atrioventricular (AV) groove of the heart. When positioned appropriately, the belt is cinched or otherwise tightened around the heart which narrows the tricuspid annulus and relieves the TR condition. To narrow the tricuspid annulus, the belt has to overcome the pressure from the heart, which may vary among patients, and which can be thought of as an unfortunate side-effect to be managed.

It has been proposed to use sutures to provide tension to the belt when necessary. Several problems have been noted with that approach. For example, when cinched the belt may generate too much pressure against the AV groove and/or coronary vessels or other tissues, which can constrain coronary flow and negatively affect heart function. Further, when a suture attached to a belt is used to cinch, it can be situated anywhere inside the belt, and move freely both axially and laterally. Control over the suture with respect to the belt, and with respect to biological structures of the heart, is thus lacking.

Overall, structures and methods for cinching a belt, and for ensuring that the belt minimizes any risk of coronary compression (e.g. compression of vessels to limit or prevent flow), are needed.

SUMMARY

Among other things, there are disclosed devices and methods for treating conditions including tricuspid valve regurgitation. Such devices include a band or belt for placement along the AV groove of the heart, which can include a heat-settable mesh tube having a first open end and a second open end and a lumen passing through the tube from the first open end to the second open end along a longitudinal axis of the tube. The tube may be configured longitudinally in a loop so as to be placed around the heart and along the AV groove. A first suture portion is within the tube, and is fixed to the tube adjacent the first open end and extends through the lumen toward the second open end. The first suture portion can be connected to the tube within the lumen by a plurality of holding elements so that the first suture portion is longitudinally movable through the holding elements with respect to the tube. In some embodiments, a second suture portion is within the tube and parallel to and spaced from the first suture portion. The second suture portion may be fixed to the tube adjacent the first open end and extend through the lumen toward the second open end. The second suture portion may be connected to the tube within the lumen by a plurality of holding elements so that the second suture portion is longitudinally movable through the holding elements with respect to the tube. Pulling the first and/or second suture portions cinches the tube to reduce an area of the loop so that the tube compresses longitudinally in at least selected locations along the tube.

In certain embodiments, the first suture portion and second suture portion each extend through the second open end of the tube to provide respective parts of the first and second suture portions that are outside the tube and able to be pulled to cinch the tube. Alternatively, the first suture portion and second suture portion can be parts of a single tensioning suture, having a middle portion between the first suture portion and second suture portion. A locking suture may be attached to the middle portion of the tensioning suture. A ring may be within the tube and adjacent the second open end, and in such cases the tensioning suture may fold over and through the ring, so that the first and second suture portions are on one side of the ring and the middle portion is on the other side of the ring. Embodiments of a ring may include a rounded engagement portion around which the tensioning suture is folded, and/or first and second linear sides that parallel the tube adjacent the second open end. The first and second linear sides may be connected to the tube by one or more respective holding elements. A locking suture can include a plurality of protrusions for use in holding tension applied to the locking suture and transmitted to the first and second suture portions. In one example, the locking suture has a length within the tube and a portion exiting the tube through the first open end, and the protrusions are on up to the full length of the locking suture within the tube and next to the first open end, and are not otherwise on the length of the locking suture within the tube.

Examples of the mesh of the tube are heat-settable materials, such as nitinol. Embodiments include the mesh being heat-set so that when the tube reaches body temperature, its cross section assumes a barbell shape, an ellipse or a flat ribbon shape. Further examples include the mesh being heat-set so that when the tube reaches body temperature, it assumes a shape with a first region having a first hoop diameter and first cross sectional dimension, and a second region having a second hoop diameter and second cross sectional dimension. The first hoop diameter may be greater than the second hoop diameter, and the first cross sectional dimension may be greater than the second cross sectional dimension. A medial portion between the first and second regions can include a contour adapted to conform to at least part of the atrioventricular groove. Another example can include the mesh being heat-set so that when the tube reaches body temperature, it assumes a saddle shape having one or more lower rounded contoured regions. At least one of the lower rounded contoured regions can be adapted to fit closely within the AV groove.

The disclosed structures minimize the risk of coronary compression as the compression belt is tensioned, and methods are disclosed to distribute applied forces of the belt over a sufficiently wide arc of the AV groove so as not to compress a coronary artery too much, while still achieving a therapeutic benefit in reducing regurgitation in the tricuspid and/or mitral valves. Embodiments of belts as disclosed herein should not exert an inward pressure (i.e. toward the heart) that is greater than coronary arterial pressure during ventricular diastole, when coronary flow is expected to be highest. Such embodiments should be shaped and/or configured to minimize any trauma to adjacent structures (e.g. no sharp edges on the belt), and to minimize risk of sliding on or around the heart once the belt is placed and cinched (if necessary). Some belt embodiments as disclosed may control the position of a suture or other tensioning element so as to optimally distribute force or pressure exerted by or otherwise associated with the tensioning element. In particular embodiments, the ends of the belt are configured to be easily pulled into a delivery catheter or other device (e.g. tapered), if retraction or correction is needed. Some belt embodiments are stretchable or compressible so as to compactly fit over a delivery frame and into a delivery catheter or other device, and will then take on a desired shape or configuration when deployed, which shape or configuration will effectively distribute tension, pressure or forces.

BRIEF DESCRIPTION OF THE DRAWINGS

FIG. 18 is a top view of an embodiment of a protective member with tensioning members.

FIG. 20A is a schematic illustration of method and apparatus for making embodiments of a protective member (illustrated in end view in FIGS. 20B and 20C).

DETAILED DESCRIPTION OF THE ILLUSTRATED EMBODIMENTS

Figure 1:
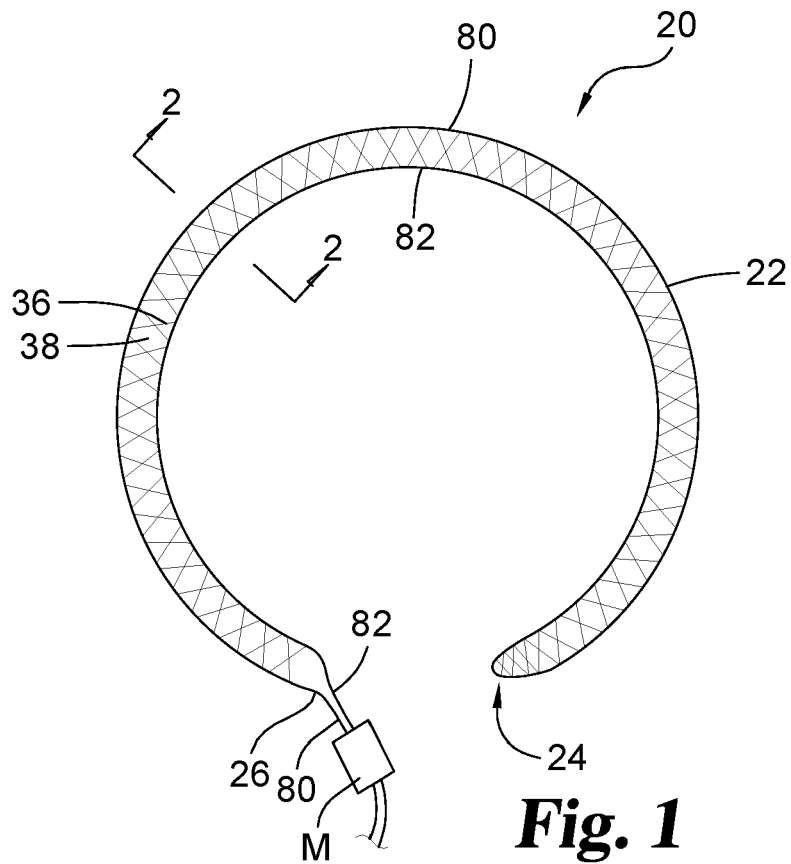
FIG. 1 is a top plan view of a belt according to embodiments disclosed herein.
Figure 2:
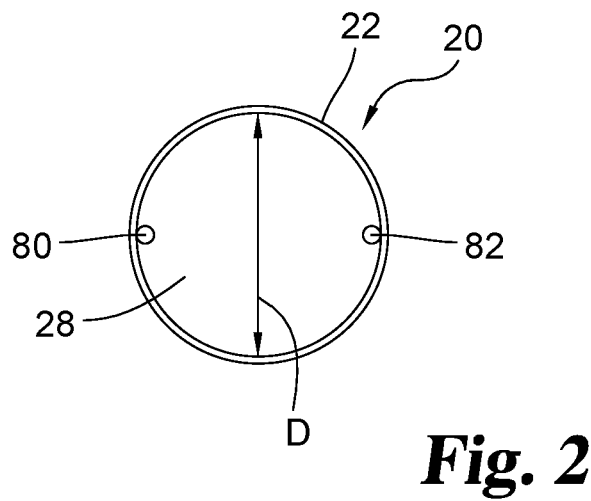
FIG. 2 is a cross-sectional view of the belt in FIG. 1, taken along the lines II-II and viewed in the direction of the arrows.
Figure 1A:
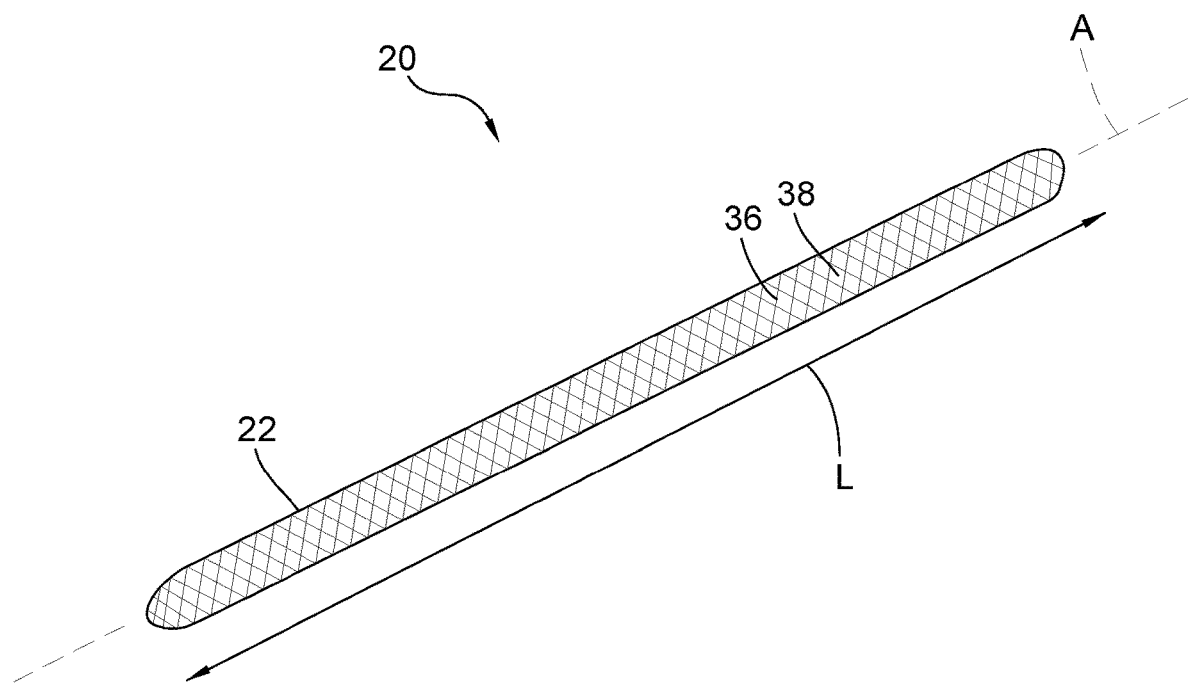
FIG. 1A is a perspective view of a mesh tube for a belt as in FIG. 1.

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the disclosure is thereby intended. Any alterations and further modifications in the described embodiments and any further applications of the principles of the present disclosure as described herein are contemplated as would normally occur to one skilled in the art to which the disclosure relates.

Referring now generally to the drawings, there is shown an embodiment of a belt 20 for use in applying compression to a bodily organ. As will be discussed below, belt 20 may be particularly prepared for application to the atrioventricular (AV) groove of the heart in treatment of tricuspid valve regurgitation (TR) conditions. While the disclosure herein may focus at times on that use and placement, it will be understood that the structures and methods disclosed may be used for a number of conditions, treatments, implants or purposes.

Belt 20 in the illustrated embodiment is a flexible mesh tube 22 of biocompatible material with opposed open ends 24, 26 and a natural diameter (i.e. a diameter that the tube has when not under stress or after being heat-set) around an internal volume or lumen 28 that extends between tapered or otherwise narrowed ends 24 and 26. One or more sutures or other tensioning members are connected to belt 20 in order to provide tension to belt 20, as will be discussed further below. Such tension can cinch belt 20 in the AV groove for treatment of TR. The mesh of tube 20 may be formed of strands, wires or fibers 36 separated by interstices 38, or by cutting, etching, stamping or otherwise treating a thin sheet to remove portions, forming interstices 38. The mesh allows belt 20 to stretch lengthwise under tension along its length or central axis A to thereby decrease its diameter in the area stretched, and to be compressed lengthwise under compression or relaxation of tension along its length or central axis A to thereby increase its diameter in the area compressed.

It will be understood that the mesh of tube 22 may be made of a number of available natural or synthetic sturdy biocompatible materials. In a particular embodiment, the mesh of belt 20 is of nitinol, for example one or more individual nitinol wires (as strand(s) 36) fixed to and/or wound about each other to form interstices 38. Belt 20 in the embodiment illustrated in FIG. 1 has an original cylindrical shape with length L and diameter D measured across the longitudinal axis A. During manufacture, or at least prior to use, embodiments of belt 20 made of a heat-settable materials (e.g. nitinol) can be heat-set into a configuration that will be assumed when deployed in the body. In that example, belt 20 has its original (e.g. cylindrical) form at room temperature, is packed for delivery, and assumes the heat-set configuration when inserted into the body and its temperature is or approaches body temperature.

As a particular example of a desirable heat-set configuration, belt 20 is shown in FIG. 3 in a heat-set flat, ribbon shape. The flat ribbon shape may be heat-set into the nitinol mesh so that belt 20 has a desired width w (from side 40 to side 42) in its deployed state to go with the initial length L. It has been determined what the width w should be set as indicated below in order to keep the pressure from belt 20 from exceeding coronary arterial pressure during ventricular diastole, for example about 30 mmHg. The stress on a cross section of belt 20 for a particular tensile force F is $\sigma_0 = F/(tw)$, where t is the thickness of the mesh of belt 20 and w is the width of belt 20 defined above. The hoop stress equation relates that stress to a desired pressure P as $\sigma_0 = Pr/t$, where t is as defined above and r is the radius of the AV groove. Setting those representations of cross-sectional stress equal to each other gives F/tw=Pr/t. Cancelling and rearranging provides w=F/Pr. With an experimentally-determined tensile force of 0.4 pounds (1.8 N), a vascular pressure of 0.58 psi (30 mmHg), and a radius of the AV groove of 2 inches (51 mm), the width w of the belt 20 is determined to be 0.35 inches (8.9 mm). It will be understood that different values for the width w of belt 20 will be determined by the above method for variations with respect to a particular patient, such as differences in the AV groove radius or differences in vascular pressure. Accordingly, a belt 20 having a width w suited to the particular patient may be custom-made. That width w is configured by heat-setting belt 20, e.g. one of braided nitinol wires, so that when heat is applied by the body (i.e. body temperature), belt 20 acquires a configuration with width w.

Figure 3A:
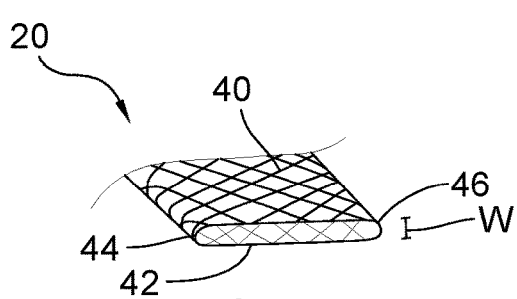
FIG. 3A is a perspective view of a cross-section of an embodiment of a belt of FIG. 1 in a particular set shape.
Figure 3B:
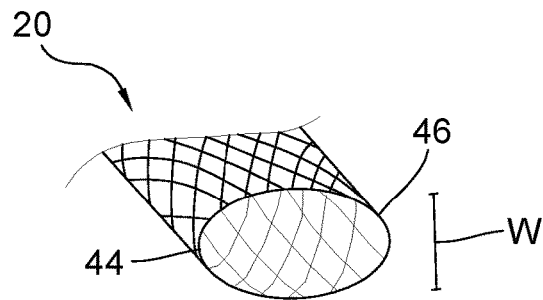
FIG. 3B is a perspective view of a cross-section of an embodiment of a belt of FIG. 1 in a particular set shape.

Preferably, belt 20 is heat-set to assume a flattened state, as in the prior example, so as to distribute the forces from the tensioning member to the belt. Flattening of the original cylindrical cross-section ranges from simply ovalizing the cross-section (FIG. 3A, a relatively high width w) to making a ribbon-like cross-section in which opposing sides 40, 42 of belt 20 are parallel to each other and closely adjacent to each other (FIG. 3B, a relatively low width w). In FIG. 3A, belt 20 is shown with an oval or elliptical cross section, with edges 44, 46 intersecting and separated by a major axis, and a middle portion between edges 44, 46, with width w being along or at least substantially parallel to a minor axis. In FIG. 3B, likewise edges 44, 46 intersect and are separated by a major axis, and width w is along or parallel to a minor axis. Edges 44, 46 provide locations for one or more sutures for tightening, as will be discussed further below.

Figure 4:
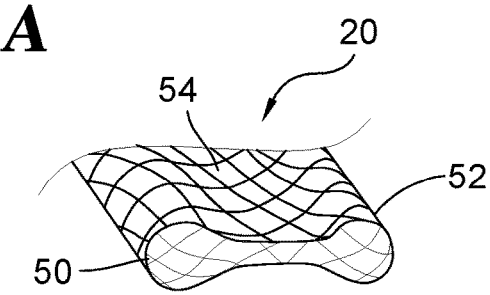
FIG. 4 is a perspective view of a cross-section of an embodiment of a belt of FIG. 1 in a particular set shape.

In particular embodiments, flattened belt 20 may be heat-set with enlarged, rounded edges 50, 52 on either side of the longitudinal axis A. In cross-section, this example of belt 20 looks like a dog bone or a barbell. As one example, the middle portion 54 of belt 20 between edges 50, 52 is flat, having the mesh at least approximately planar in each side 40, 42 between edges 50, 52, with those sides 40, 42 close to or touching each other side. Edges 50, 52 are round or curved, for example having a circular or oval cylindrical cross-section. In some illustrated embodiments (e.g. FIG. 4), edges 50, 52 have the same configuration as each other. Enlarged edges 50, 52 provide additional surface area to engage and grip the underlying tissue in the AV groove. Edges 50, 52, since they are rounded, reduce the potential for sharp corners or other surfaces that may cause any trauma to adjacent heart tissue. Since appendages or lobes of the atria may overhang belt 20 in the AV groove, a lack of such surfaces is preferred.

Figure 5:
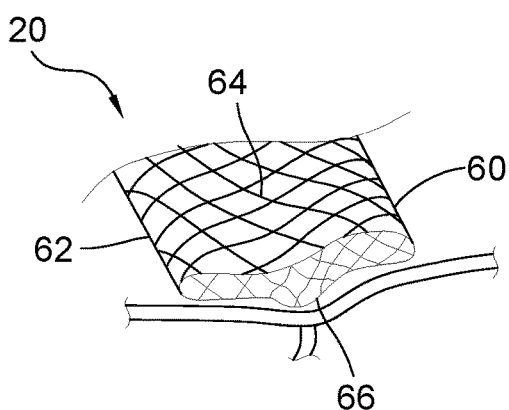
FIG. 5 is a perspective view of a cross-section of an embodiment of a belt of FIG. 1 in a particular set shape.

In another embodiment, belt 20 is heat set with a cross-section that creates a region 60 with a larger hoop diameter on one side, and a region 62 with a tighter/smaller hoop diameter. Region 60 is designed for placement over the ventricular walls, which are thicker than atrial tissues, and also have a higher chamber pressure. The thicker cross-section of region 60 has the advantage of more secure hold to the ventricular tissue, and the higher chamber pressure will withstand that thicker material. Region 62 is designed for placement over the thinner AV groove and atrial walls with their lower chamber pressure. The thinner region 62 can allow a medial portion 64 of belt 20 to more closely fit in the AV groove. Medial portion 64, as seen in the example of FIG. 5, can include a contour 66 in side 42 that conforms to at least part of the AV groove.

In another embodiment, belt 20 is heat-set with a ring shape with or approximating a natural curve of the exterior of the heart, so that belt 20 can have a natural location or fit around the heart. For example, an image of the heart may be taken so as to model the organ, and that imaging used to create a curve in belt 20, which is then heat-set into belt 20. Such an embodiment eases deployment, as belt 20 will assume the shape of the heart when deployed. A belt 20 in that shape will fit better over the heart, akin to fitting an oval peg into a hole with corresponding size and shape, and will conform better to the contours of the heart prior to a final tensioning of belt 20.

Figure 6:
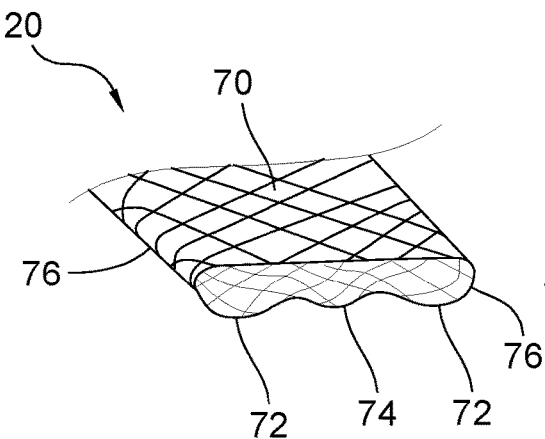
FIG. 6 is a perspective view of a cross-section of an embodiment of a belt of FIG. 1 in a particular set shape.

In another embodiment, belt 20 is heat-set with a three-lobed or saddle shape. FIG. 6 is an example cross sectional shape that would allow the passage of three sutures, e.g. one along each lobe, so as to distribute the load laterally along the AV groove. The shape addresses the fact that the AV groove itself does not lie in a single plane. A shape of belt 20 as in FIG. 6 allows it to more naturally sit in the AV groove upon deployment. Further, when used with three tensioning sutures, the lobes keep the sutures separated and distribute the compressive forces applied by the sutures. In that example, belt 20 has an upper flat region 70 and one or more lower contoured regions, e.g. two side lobes 72 and a middle lobe 74. Middle lobe 74 is rounded, e.g. part-cylindrical or a rounded ridge, that is adapted to fit within, and preferably closely within, the AV groove. Side lobes 72 are rounded, e.g. with at least part having essentially the same curvature as middle lobe 74, and edges 76 are also rounded. Such edge regions, as noted above with respect to (dog-bone version), provide more secure engagement without sharp corners. More generally, the pathway of belt 20 can be heat set to a non-planar three-dimensional shape that better traces the pathway of the AV groove in the heart.

In any of these embodiments, belt 20 may be heat-set to provide a greater width w of belt 20 for regions of the belt that are to be placed over areas of the heart where arteries are (more likely) to pass underneath. That greater width allows for a relatively smaller pressure in that area of belt 20 when tensioned, and such an area should be over regions of the heart where arteries pass. Belt 20 may be narrower in width in portions that will lie over or near the tricuspid annulus of the heart. That narrower width may provide a relatively greater pressure in that area of belt 20 when tensioned, and thus directs that greater pressure where needed to treat tricuspid regurgitation.

In any of the embodiments of belts disclosed herein, tension is applied by one or more sutures through the belt. By "sutures" is meant not only the common definition, but any biocompatible line or filament having flexibility and tensile strength sufficient to be passed through a belt for use in procedures such as TR treatment and pull in tension when deployed, as discussed herein. Further, "sutures" means not only wholly separate items but also portions of one or more such items. Pulling or otherwise placing the suture(s) in tension applies compression to the belt, thereby applying compression to the AV groove of the heart.

Figure 7:
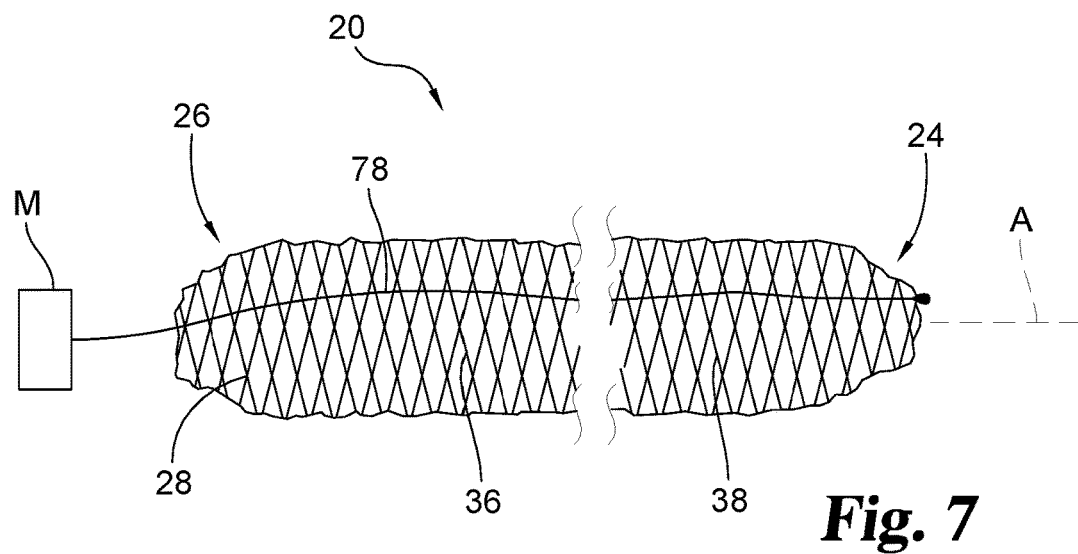
FIG. 7 is a plan view of an embodiment of a belt with a single tensioning suture.

In embodiments in which only one tensioning suture is attached or otherwise connected to belt 20 (e.g. FIG. 7), the suture 78 may float within belt 20 through lumen 28. One end of the tensioning suture 78 is fixed to belt 20 at or near one end 24 of belt 20 (and a locking mechanism M attached or otherwise connected to belt 20) in particular embodiments. The suture 78 passes through lumen 28 and out of end 26 of belt 20 and through the locking mechanism M. The tensioning suture 78 within belt 20 can move both axially and laterally with respect to belt 20. Pulling on the end of the tensioning suture 78 that passes through the locking mechanism, with the other end fixed to belt 20, moves part of the suture 78 through belt 20. End 24 is pulled along axis A along with suture 78, to reduce the length of belt 20 and placing it in tension. Activation of the locking mechanism M holds the suture 78, and belt 20, with that tension around the heart.

Figure 8:
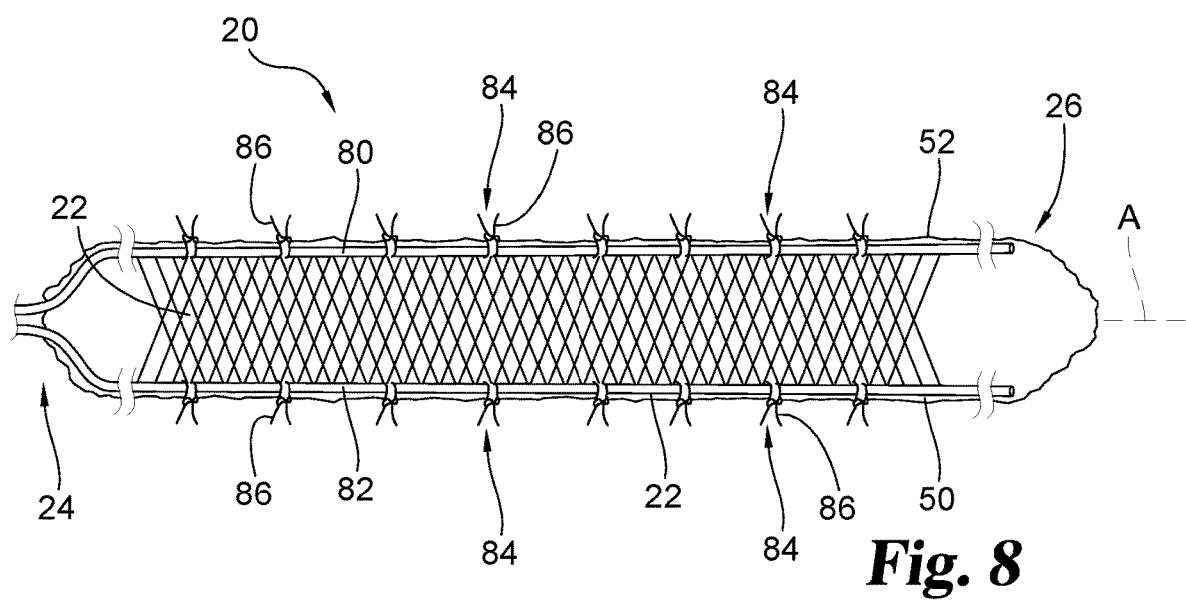
FIGS. 8-10 are plan views of embodiments of a belt with two tensioning suture portions.

In the embodiment illustrated in FIG. 8, belt 20 includes two parallel sutures or suture portions 80, 82 within it to provide tension. It has been found that the use of two sutures 80, 82 is more effective in providing steady tension to belt 20, and in distributing the pressure or force when cinching or tightening belt 20 around the heart, than can be done with a single suture floating within belt 20. For example, application of force through two separated sutures reduces or eliminates risk of turning or pivoting of belt 20 during tightening or cinching, e.g. by turning belt around an edge (e.g. 44, 46, 50 or 52) so that flat belt 20 rises or stands on one edge. It has also been found that use of two sutures 80, 82 with belt 20 is more effective when sutures 80, 82 are confined laterally, i.e. maintained apart from each other. It has been found that two floating sutures tend to stay together, due to minimized potential energy, or being pulled together during deployment or cinching of belt 20. When the sutures stay together, they tend to behave like a single, thicker suture, which loses the force application and distribution and other benefits of having two sutures.

Figure 10:
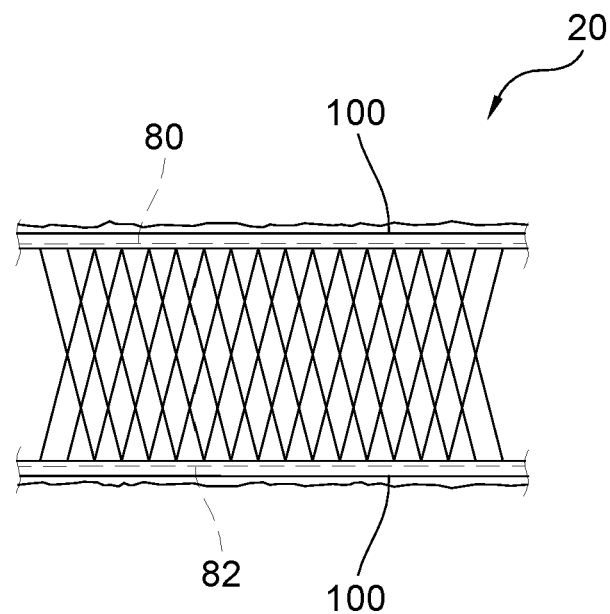

Sutures 80, 82 are attached to belt 20 in locations opposed to each other across the longitudinal axis of belt 20, and in the illustrated embodiment, sutures 80, 82 are attached to the inside of belt 20. In embodiments in which belt 20 is heat-set to a particular shape, sutures 80, 82 are placed after heat-setting. A series of holding elements 84 surround sutures 80, 82 in various locations along belt 20. In a particular embodiment, elements 84 are threads or filaments that tie around the respective suture 80, 82 and through the mesh of belt 20. For example, a holding element 84 in the form of a filament 86 is threaded through the mesh, around suture 80, and back through mesh, one or more times, and then is knotted, heat-fused, or otherwise secured. In the illustrated embodiment, filament 86 is threaded or looped around suture 80 at least twice, and secured at or adjacent belt 20, e.g. on an outer surface of belt 20. It will be understood that securing (e.g. by knotting) filament 86 with respect to itself and to belt 20 retains some slack or flexibility in filament 86 to form an opening or passage 88 through each holding element 84 that allow suture 80 to move longitudinally through the passages 88 of respective holding elements 84 with minimal resistance. As a particular case, a respective tube for each respective tensioning suture 80, 82 may be placed through the lumen of belt 20, similar to tube 100 shown in FIG. 10. The respective tensioning suture extends through its respective tube either initially or by being threaded through after the tube is placed within belt 20. Filaments 86 can be threaded through the mesh of belt 20 and around the tube, for example twice or more, cinched to be snug around the tube and knotted or otherwise secured, to form securing elements 84. Then the tube may be slid out from elements 84 over the respective tensioning suture. The snug fit of elements 84 around the tube makes tying or fixing the elements easier, and ensures that the elements are slack with respect to the tensioning suture when the tube is removed. Similar or identical holding or securing elements 84 are present for suture 82.

In other embodiments, holding elements may be or include rings, tubing or sheath attached to belt 20. Filaments as discussed above behave as rings. In an example of belt 20 made of nitinol wires in a mesh, internal guide rings (92 in FIG. 9) may be formed using the individual wire(s) that form the mesh of belt 20 (e.g. such rings may be created when the mesh for belt 20 is formed). Rings 92 have an opening or passage 94 sized to allow suture 80 or 82 to pass through rings longitudinally with minimal resistance. The metallic surface of rings 92 may provide significantly less resistance to longitudinal passage of sutures 80, 82 than filament holding elements 84, particularly if the metal (e.g. nitinol wires) are smoothed, as is indicated for use in belt 20 so as to limit or eliminate damage or irritation to adjacent tissue. In other embodiments, a tube or sheath 100 may be attached to the inside of belt 20 (e.g. FIG. 10), in similar locations to individual filament holding elements 84 or ring holding elements 92, which have a passage sized to allow suture 80 or 82 to pass through rings longitudinally with minimal resistance. Several individual tubes may be placed within belt 20 and separated by gaps from each other, particularly if such tubes are less longitudinally compressible than belt 20, or if a single tube 100 is used as a holding element, such a tube should be compressible so as not to limit the cinching of belt 20 when placing it in tension.

Securing or holding elements 84 are evenly spaced, in the illustrated embodiment, along belt 20. Because sutures 80, 82 are intended to remain in tension or essentially linear in holding elements 84 along belt 20, holding elements 84 may be spaced relatively far from each other, e.g. up to 5 millimeters, up to 10 millimeters, up to 15 millimeters, up to 20 millimeters from each other in particular embodiments, or close enough to each other so that any slack that may exist in one or both of suture 80, 82 does not allow one of sutures 80, 82 to touch the other when belt is being deployed. Further, the locations of holding elements 84 are shown in one embodiment as staggered along sutures 80, 82, i.e. a plane perpendicular to the longitudinal axis of belt 20 through one holding element 84 holding one suture 80 will pass between holding elements 84 holding the other suture 82, and in a particular embodiment will be halfway between holding elements 84 holding the other suture 82 (e.g. FIG. 8). That staggered condition allows belt 20 to be folded, compressed or otherwise packed into a delivery device with holding elements 84 offset from each other, providing a lower profile for the delivery device. In other embodiments, holding elements 84 may be symmetric or only very slightly offset (e.g. by 1-3 millimeters, so that the above noted plane through a holding element with suture 80 may pass immediately next to a holding element with suture 82) in belt 20.

In such a case, tension by sutures 80, 82 is applied to belt 20, via holding elements 84, at or near the same locations on sides 40, 42 of belt 20.

In other embodiments, one or both of sutures 80, 82 may be woven through the mesh of belt 20 along two lines each lateral of the longitudinal axis of belt 20. In one example, suture 80 may be fixed at one end 24 of the interior of belt 20, passed out through the mesh of belt 20 and run along the outside of belt 20 for a length, then passed back through the mesh to the inside of belt 20 for a length (which may be the same or a different length as was run along the outside of belt 20). That weaving continues through the length of belt 20. Suture 82 may be similarly or identically woven through the other side of belt 20. It has been found that such weaving produces relatively high friction forces between suture(s) 80, 82 and belt 20, and when suture(s) 80, 82 are cinched, the tension provided to belt 20 may not be homogeneous, so that part of belt 20 contracts around the heart, while other parts may remain relatively loose. Thus, weaving suture(s) 80, 82 through belt 20 may be effective under certain circumstances, but other embodiments disclosed herein operate in a more effective fashion.

Figure 11:
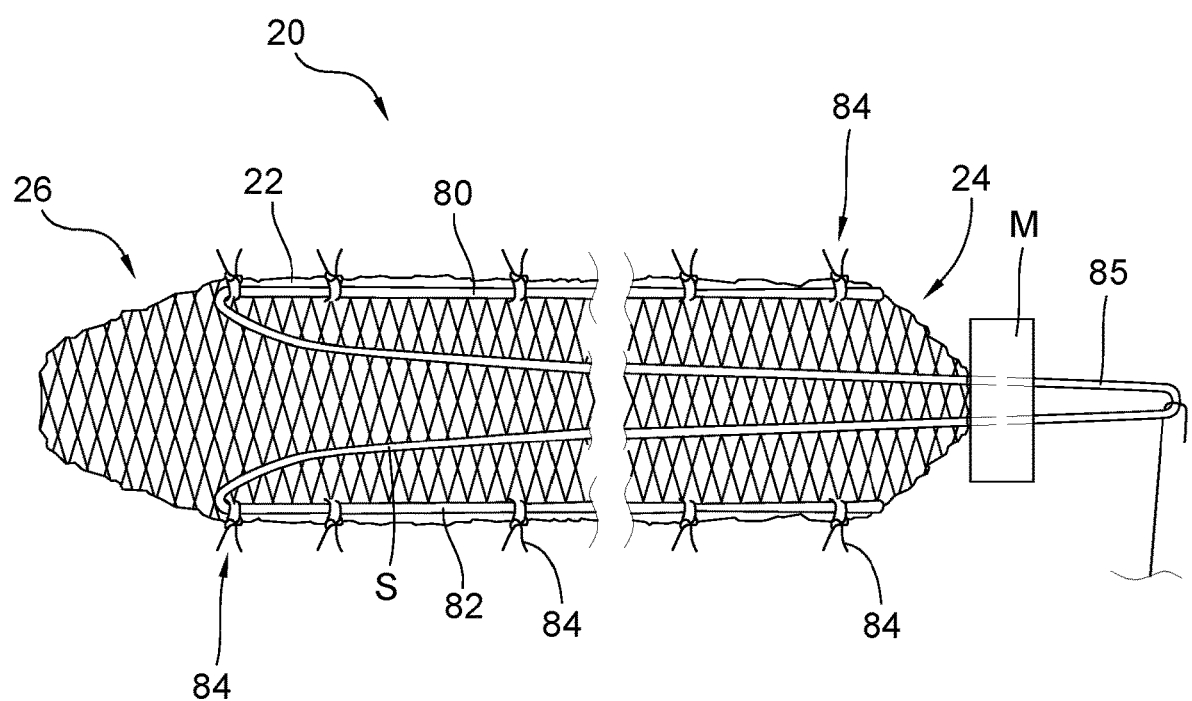
FIG. 11 is a plan view of an embodiment of a belt with two tensioning suture portions with a middle loop.

In another embodiment, shown in FIG. 11, a belt 20 is shown that is similar or identical to embodiments of belt 20 described above, including mesh tube 22 with narrowed ends 24, 26. In this embodiment, a single suture S extends through belt 20, with a first suture portion 80 extending along one side or edge of belt 20 and a second suture portion 82 extending along an opposite side or edge of belt 20. As with other belt embodiments described herein, suture S is fixed to tube 22 at end 24, e.g. an end of suture portion 80 and an end of suture portion 82 are respectively fixed to tube 22, as indicated in FIG. 11, or to a locking mechanism M adjacent or connected to tube 22. From those fixed ends, each suture portion 80, 84 runs toward end 26, and are held to tube 22 by one or more holding elements 84, as discussed above. When suture portions 80, 82 are near or reach end 26 in this embodiment, suture S loops back through lumen 28 of belt 20 to form loop 85. Loop 85 in this embodiment extends through lumen 28 and out through end 24 (and through locking mechanism M, if present) to an exterior of tube 22 of belt 20. Loop 85 can be connected to a tensioning line T, as by a hook, grip or other structure, that may be part of a system for delivering belt 20. Following deployment of belt 20, as generally described below, tensioning line T can preferably be disengaged from loop 85 and withdrawn. This embodiment provides redundancy, so that if one of suture portions 80, 82 fails, the other suture portion remains to provide tension to belt 20.

In another embodiment, belt 20 (FIG. 12) is configured the same as embodiment(s) above, with holding elements 184 that are similar or identical to holding elements 84 described above. It will be understood that belt 20 may be made, shaped and/or configured as described above with respect to particularly-shaped or set embodiments. A first suture or suture portion 180 passes through holding elements 184 along one side 140 of belt 20, and a second suture or suture portion 182 passes through holding elements 184 along another side 142 of belt 20, e.g. a side opposite from suture or suture portion 180 across the longitudinal axis A of belt 20. A locking suture 210 is connected to suture portions 180, 182 at or adjacent one end 226 of belt 20, and the suture portions 180, 182 pass through a ring 212 at or adjacent that end 226 of belt 180.

Figure 12:
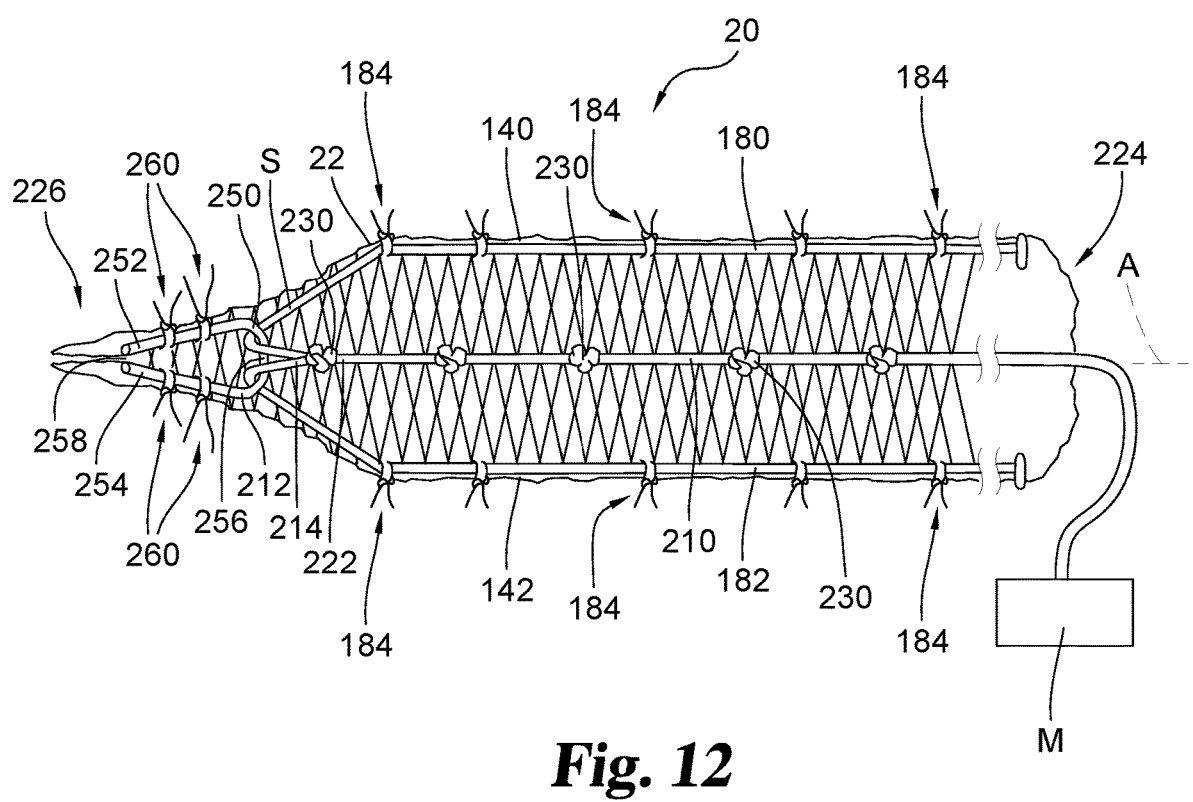
FIG. 12 is a plan view of an embodiment of a belt with two tensioning suture portions with a middle loop and additional structure.

In the illustrated embodiment, suture portions 180, 182 are part of a single tensioning suture S. Suture portions 180, 182 are each fixed to end 224 of belt 20 (e.g. by a blanket stitch), as described above with respect to suture 80, 82. Suture portion 180 passes through holding elements 184 on one side of belt 20 (e.g. the top as seen in FIG. 12), then a central loop 214 of the suture S passes through ring 212 at or near the other end 226 of belt 20, and the rest of the suture S passes through holding elements 184 on the other side of belt 80 (e.g. the bottom as seen in FIG. 12) and is fixed at end 224 of belt 20. Loop 214 that passes through ring 212 is fixed to an end 222 of locking suture 210, so that the tensioning suture S folds over a portion of ring 212 (i.e. bending 180 degrees around and through ring 212), with portions 80, 82 on one side of ring 212 and loop 214 on the other. It will be understood that in other embodiments suture portions 80, 82 may be separate tensioning sutures, each of which pass through ring 212 as described above and attach to locking suture 210.

Locking suture 210 in the illustrated embodiment includes a series of knots, beads or other protrusions 230, which in the illustrated embodiment are evenly spaced along the whole length of suture 210 within belt 220 and into a locking mechanism M (as described above). In other embodiments, protrusions 230 may be present only in part of suture 210, e.g. of the part of locking suture 210 within belt 220 and into locking mechanism M, at least the one-third to one-half that is furthest from ring 212. It has been found that the tensioned or cinched belt (e.g. belt 20) may need to have a length between 60 and 80 percent of the initial length L of the belt, and so a length of suture 210 (e.g. between 80 and 40 percent of the initial length of suture 210 within the belt) will have to pass out of the belt and to or through a locking mechanism M. Accordingly, placing protrusions on at least the 40 to 80 percent of suture 210 that is adjacent mechanism M and entering belt 20, and therefore has the potential to be pulled through the end of the belt and a locking mechanism, is advantageous.

Ring 212 in the illustrated embodiment has a rounded (e.g. circular) portion 250 over which tensioning sutures or suture portions 180, 182 are folded, and two linear sides 252, 254 that join to each other and to rounded portion 250. Ring 212 may be made of a biocompatible wire or other sturdy material, and is relatively inflexible so as to be able to effectively transfer tension from locking suture 210 to tensioning suture portions 180, 182. The exterior surface 256 of ring 212 is rounded (e.g. made of wire that is circular in cross section) and smooth in certain embodiments, so as to reduce friction between ring 212 and tensioning suture portions 180, 182 during use. It has been found in experimental testing that the cross-sectional diameter of wire used in embodiments of ring 212 has a substantial effect on friction between ring 212 and suture portions 180, 182, and that for a suture of 0.35 millimeter diameter and made of ultra-high molecular weight polyethylene (UHMWPE), wire used to make ring 212 should have a diameter of 0.021 inches or larger.

Sides 252 and 254 are unitary or monolithic with rounded portion 250, and are linear in this embodiment, joining with each other at an apex 258. The linear nature of sides 252, 254 is intended to fit closely with the narrowing sides 240, 242 of belt 20 at end 226 of belt 20, and in a particular embodiment the angle between sides 252, 254 at apex 258 is between 5 and 30 degrees. Sides 252, 254 may be initially separate and be joined at apex 258, as by welding, adhesives or other techniques, or they may be formed joined with each other and with rounded portion 250. Ring 212 is held to the narrowing sides 240, 242 of belt 20 by holding elements 260, which may be similar or identical to embodiments of holding elements 84 described above.

The embodiment of belt 20, with ring 212, provides several advantages, including low friction between the tensioning suture 180, 182 and belt 20, and a locking suture 210 having protrusions 230 that has a low risk of becoming stuck to belt 20. The design will permit cinching of belt 20 up to about 50 percent of the original length of belt 20, which will provide sufficient decrease of tricuspid annulus in TR treatment. Also, as noted above with respect to FIG. 11, a failure in one suture 180 or 182, leaves the other to provide tension to belt 20.

Use of belt 20 will now be discussed in the context of placement in or along a patient's AV groove and tightening, for treatment of TR or other conditions. It will be understood that use of the disclosed structure in other locations or contexts is possible. Reference in the following discussion is particularly to the embodiment in FIG. 12. However, it will be understood that the methods described below are generally applicable to other embodiments of belt 20 described herein, the principal difference being the lack of ring 212 and/or a locking suture 210.

Belt 20 is delivered to the AV groove, as by a delivery system (not shown) that can include an introducer as disclosed in PCT/US2017/058245, filed Oct. 25, 2017, which is incorporated by reference herein in its entirety. Belt 20 exits the delivery system and is looped around the heart, and situated in the AV groove. Belt 20 and suture portions 180, 182 thus circle around the heart.

When placement of belt 20 is determined to be satisfactory, the user proceeds to tighten belt 20 to decrease tricuspid annulus on the heart around the AV groove. The user pulls on locking suture 210 using an appropriate tool (not shown), so that locking suture begins to exit end 224 of belt 20 and move through locking mechanism M. As locking suture 210 is pulled, loop 214 is also pulled, and tension in locking suture 210 is passed around ring 212 to tensioning suture portions 180, 182. Suture portions 180, 182 are thus pulled through their respective holding elements 184. Pulling suture portions 180, 182 reduces the radius of suture portions 180, 182 around the heart, forcing belt 20 inward against the heart, and the respective ends of suture portions 180, 182 that are fixed to end 224 of belt 20 compress the length of belt 20. As the length of belt 20 is compressed, the mesh of belt 20 transmits that compression into some expansion in width, providing flexibility so as to limit or reduce pressure exerted on coronary arteries or other structures.

Locking suture 210 is pulled until the desired amount of tricuspid annulus decrease is achieved. In particular embodiments, as noted above, that amount is achieved with a reduction in length of belt 20 to up to 60 percent of the original length of belt 20. Once the cinching or tightening is complete, locking mechanism M is activated to hold locking suture 210 in the tensioned condition. Removal of delivery and other tools and completion of the procedure can then be performed.

Structures or other features specified in the above clauses may be included singly or in any combination in the inventive devices, along with other structures or features described above with respect to any embodiment.

Along the lines of the devices described above, similar or identical devices can be used in treatment of bodily organs or tissues in an open-surgical environment, and particularly (but without limitation) in treatment of the heart. That is, a surgically-delivered annuloplasty device is disclosed for placement on the epicardial surface of the heart, e.g. around the AV groove, with the device delivered through a surgical, open-chest approach. For instance, after exposing the epicardial space via a sternotomy or thoracotomy, the device is placed and secured around the heart. The device can be tightened to constrain the annular dimensions of one or both of the tricuspid and mitral valves. By constraining these dimensions, valve leaflets are pulled closer together, allowing them to better seal and reducing regurgitation through either valve.

In the discussion below, devices having features similar or identical to the sutures or other tensioning elements 78, 80, 82, 180, 182 and/or belts 20 around those elements described above are described. It will be seen that devices as described above can be used with an open surgical approach. The following embodiments have been developed with particular focus on such an approach, although it will be seen that they (or features of them) can be used with other approaches, or with other embodiments described herein.

At its base, devices as described below (beginning with the embodiment of device 300 illustrated in FIG. 13) includes a tensioning member 302 that wraps around the heart, preferably at the level of the AV groove. Tensioning member 302 is preferably a high-strength surgical suture material such as braided suture made from high molecular-weight polyethylene, but may be made from other materials such as wire, other surgical suture material, a braided ribbon of such materials, a fabric band of biocompatible or bio-resorbable fabric, or a bio-resorbable material such as resorbable suture or a band constructed with biological product such as small-intestinal submucosa (SIS) tissue. Tensioning member 302 can be tightened or shortened to provide additional tension or pressure on the heart, or loosened or lengthened to relieve such tension or pressure. In that way, the amount of constraint on the annular dimensions of the heart, and the valve(s) needing therapy, can be controlled.

In particular embodiments, tensioning member 302 is used without a cover, belt (e.g. embodiments of belts described above) or other protective member. With an open surgical procedure, the surgeon may simply manipulate the tensioning member 302 so that it surrounds the heart (indicated schematically by H in FIG. 13), e.g. placing it over or in the AV groove. For instance, using existing tools (such as gripping tools like hemostats or threading tools like needles) and/or the hands, the surgeon can wind or thread tensioning member 302 around the heart manually. Holding tensioning member 302 in tension around the heart can be done by knotting it, and/or with a holding piece or tool as described below. As tensioning member 302 is tightened around the heart, excess slack is gathered at the junction of the two ends 304, 306 of tensioning member 302. This excess slack may pass through a lock or buckle (discussed further below) and be allowed to gather in the pericardial space around the heart. It also may be trimmed with a cutting tool once the desired amount of force or constraint is established around the heart.

Figure 13:
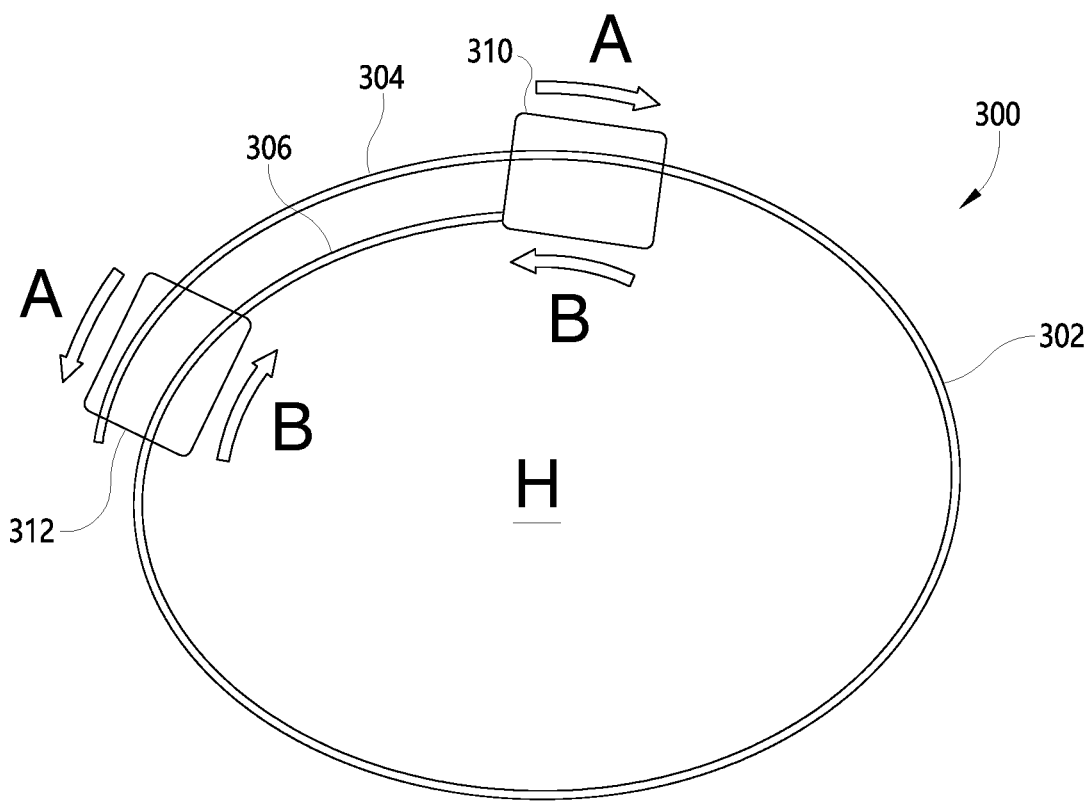
FIG. 13 is a schematic illustration of an embodiment of a tensioning member.
Figure 17:
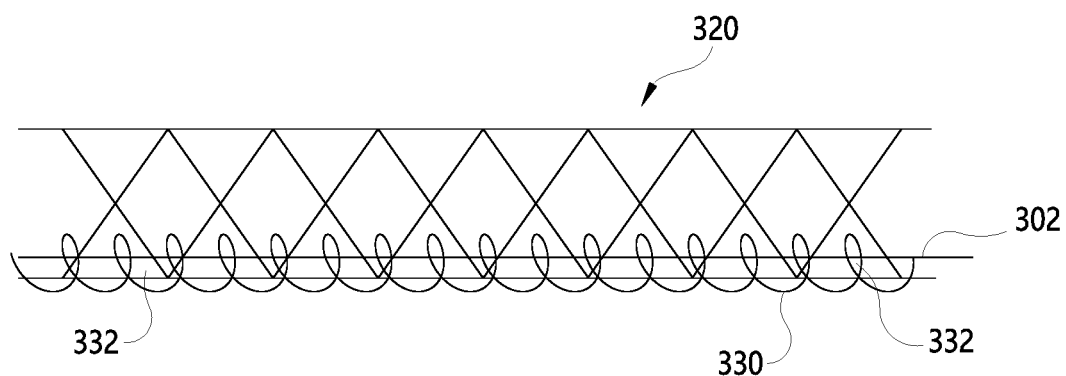
FIG. 17 is a partial side view of an embodiment of a protective member with a tensioning member.

In the embodiment of FIG. 13, each end 304, 306 of tensioning member 302 is fixedly attached to a respective buckle 310, 312. Each buckle 310, 312 then slides along the opposite end of the tensioning member 302, e.g. buckle 310 slides along end 304, and buckle 312 slides along end 306. As the buckles 310, 312 are pushed apart with respect to each other (indicated by arrows A), the tensioning member 302 is drawn tighter, shrinking the area circumscribed by the tensioning member and adding force or constraint to the heart. Conversely, as buckles 310, 312 are drawn together (arrows B), tensioning member 302 loosens, expanding the area within the tensioning member and reducing or eliminating force on the heart. One or more tools may be provided to hold, guide or provide force to one or both buckles 310, 312 in drawing them apart or pushing them together to adjust tension, while minimizing any lateral forces applied to the heart.

Figure 14:
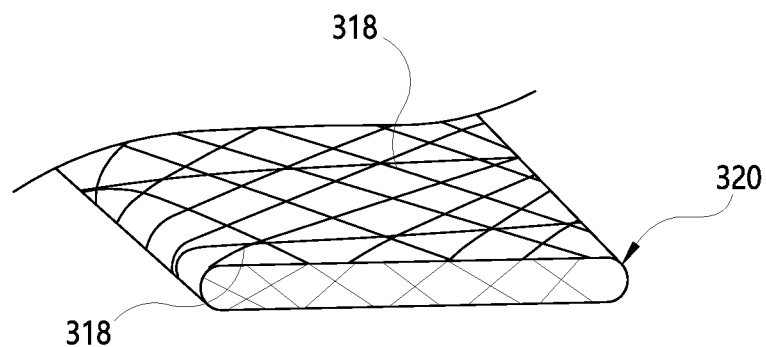
FIG. 14 is a partial perspective view of an embodiment of a protective member.

Tensioning member 302 is preferably designed to broadly apply load to the outside surface of the heart. Accordingly, it may be of a shape or structure that is significantly wider than it is tall, for example a widened structure like a ribbon or band (as described above with respect to examples of FIGS. 3-6). Such a ribbon or band may have lateral stiffness sufficient to prevent or inhibit twisting during use, to ensure it contacts the heart with its widened dimension, not a narrow edge. As one example, tensioning member 302 may be woven with or have molded within or to it lateral stiffening members 318 (shown as ribs in FIG. 14) to provide such lateral stiffness. Ribs 318 may extend part-way or all the way along a top and/or bottom portion of tensioning member 302. Stiffness of individual ribs 318 may be greater than or similar to that of tensioning member 302. Ribs 318 prevent or minimize the ability or chance of a side of tensioning member 302 to fold over, or of the whole turning onto a narrow edge, by increasing the torque needed to do so.

Figure 15:
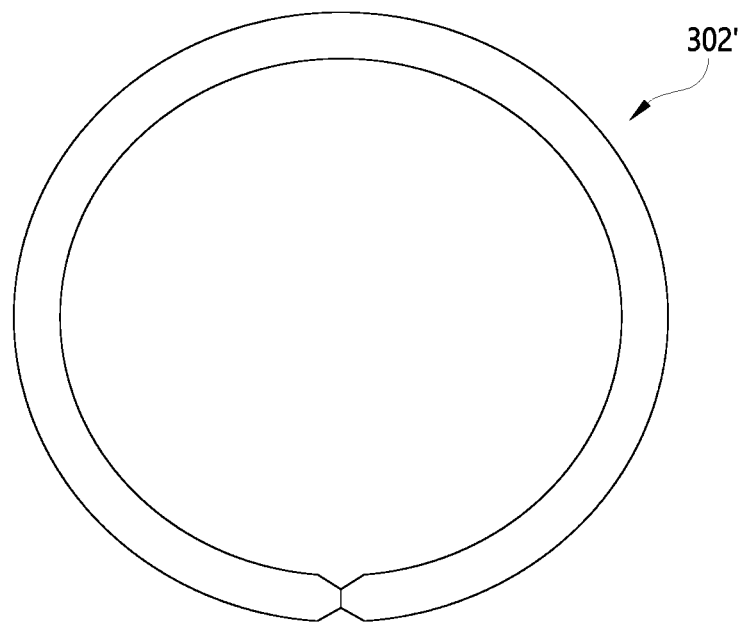
FIG. 15 is a top view of an embodiment of a protective member.

In a particular embodiment (FIG. 15), a tensioning member 302' is an elastic fiber structure having a natural unstressed diameter or internal dimension, but can be stretched or expanded to a larger dimension for placement around the heart. In that embodiment, tensioning member 302' may be a complete loop, as initially formed or with ends that are pre-connected. Tensioning member 302' would be pre-selected based on a patient's heart size so as to elastically constrain the heart after placement. Tensioning member 302' would be expanded during placement around the heart as the surgeon desires, remaining around the heart at or somewhat larger than its initial unstressed dimension, thereby engaging and placing force on the heart tissue. Elastic material for this embodiment may include a structure braided from nitinol, which is heat set to a shortened state but stretchable to a larger state when placed around the heart.

Figure 16:
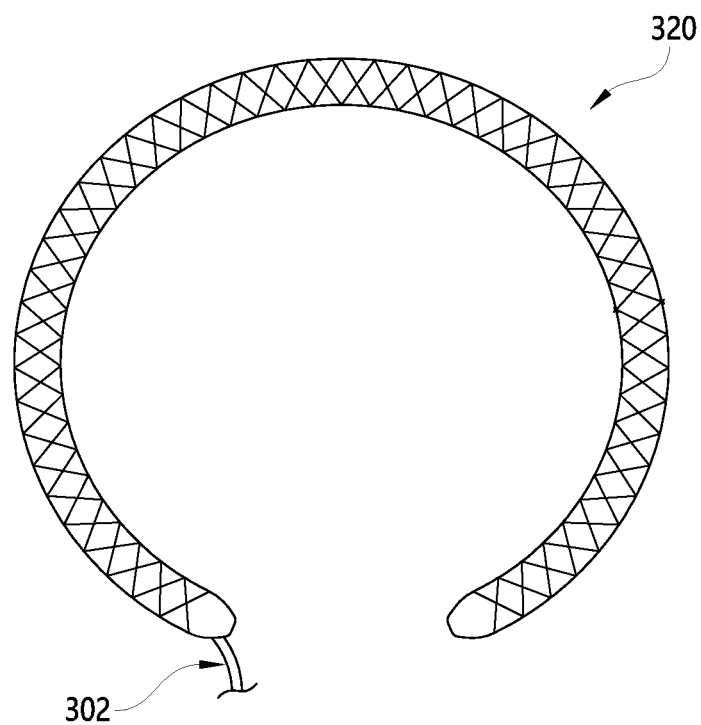
FIG. 16 is a top view of an embodiment of a protective member.

As previously noted, a tensioning member is usable by itself in a open-surgical procedure. In some embodiments, a tensioning member (e.g. a suture as discussed above or tensioning member 302, 302') may pass through a belt 20 (as described above) or other protective member 320 (e.g. FIG. 16). Protective member 320 in the following discussion may be or include features of belts 20 described and shown above. For example, beyond tensioning member 302, 302' passing through protective member 320, protective member 320 can shorten or lengthen to provide complete coverage over the entire length of tensioning member 302, even as the length of tensioning member 302 is shortened or lengthened (with associated constriction or expansion of area circumscribed by tensioning member 302) to adjust to heart size and/or degree of constraint desired by the surgeon. A mesh belt, as described above, expands or contracts in length (e.g. widening as it shortens) to better spread the contact force applied to the heart or organ and can be used as protective member 320.

In particular embodiments, like embodiments of tensioning member 302 described above, protective member 320 is made of a memory material that resists twisting, and tends to maintain a widened dimension of the protective member (rather than a narrower edge) to remain in contact with the heart. Protective member 320 is preferably easily visible in any of a number of imaging modalities, such as fluoroscopy, CT scanning, ultrasound imaging, and/or magnetic resonance imaging. With particular respect to MRI, embodiments of protective member 320 may be of a material that does not result in localized heating or generation of stimulating electrical fields during a scan. To do so, protective member 320 may be made of non-conductive materials and be coated to prevent such effects.

As with belt 20 described above, protective member 320 may have one or more tensioning members as discussed above extending through it. Protective member 320 has guide members in particular embodiments to guide a single tensioning member or multiple tensioning members within protective member 320. The guide members may hold the tensioning members at opposite ends of the cross section of protective member 320 (see FIGS. 8, 9, 11, 12), which as discussed above allows better distribution of the applied forces of the tensioning members 302. When protective member 320 widens, multiple tensioning members 302 are spread further apart.

Figure 9:
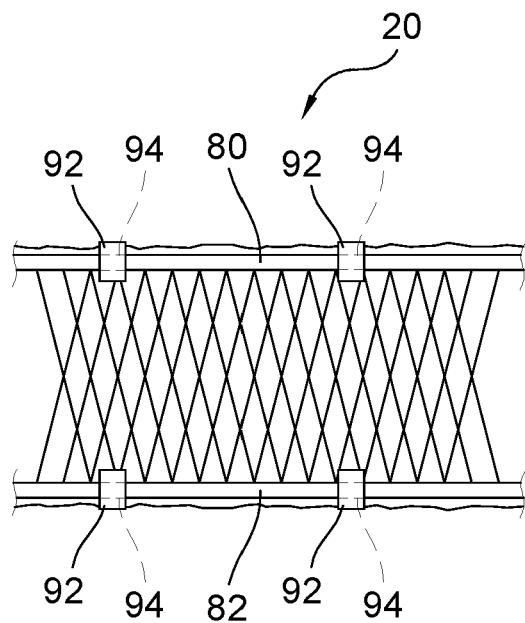

Such guide members may be identical or similar to structures discussed above and shown in FIGS. 8, 9, 11, 12. For example, they may be suture loops (FIG. 8, 11, 12) or rings attached to points on the protective member (FIG. 9). In other embodiments, protective member 320 may have guide loops that are heat welded or heat set into structure (e.g., in a braided structure, to one or more of the braided filaments) to allow the tensioning members to easily pass through. Such heat-set guide loops may be situated as the suture loops seen in the above-noted figures. As a further alternative, protective member 320 may have a guide coil 330 wound through it to allow passage of a tensioning member 302. Coil 330 defines a lumen 332 as it winds through the filaments or material of protective member 320, and a tensioning member 302 may pass through lumen 332.

Several possible treatments (mechanical, chemical, or by application of compositions) are contemplated for a tensioning member and/or protective member. For example, the entirety (or at least the heart-contacting surface) of a tensioning member (e.g. tensioning member 302) and/or protective member (e.g. belt 20 or other protective member 320) may be treated to promote tissue ingrowth. The surface may be textured or have a Velcro-like loop structure that encourages tissue to grow onto or into the surface. As another example, a surface (e.g. the pericardial surface) may be treated to prevent adhesion of the pericardium, as by being smooth and/or made of a material or having a coating that resists tissue in-growth. As a further example, one or both of the tensioning member and protective member may be treated or coated with an antimicrobial agent to create infection resistance, or with an anti-inflammatory agent to resist inflammation and creation of pericardial adhesions.

The above-described embodiments of protective members (including belt 20) are single units, with ends that are either separated for tightening or joined to form a continuous ring. In the embodiment shown in FIG. 18, protective member 420 is split into two ring halves 422, 424, but is otherwise consistent with embodiments discussed herein. That is, each half is constructed in a manner disclosed herein, for example a mesh tube with a lumen, and each half has its own suture(s) or tensioning member(s) 426, 428. The two halves 422, 424 allow independent control by the surgeon of protection and constraint around the respective right and left sides of the heart. As seen in FIG. 18, tensioning members 426, 428 form respective loops within ring halves 422, 424 and engage the respective ring halves in a manner that allows tensioning and constraining of each around a portion of the heart independently of the other.

The two halves 422, 424 may join at the locations of the heart (indicated schematically by H in FIG. 18) where the right heart RH borders the left heart LH. Anchors 430 to the heart may be placed at these joints or locations, and preferably with each half 422, 424 anchored to the heart independently of the other, to secure halves 422, 424 to the heart. Anchors 430 may be sutures, or alternatively be small corkscrew-like anchors known for anchoring soft tissue, that can be inserted into the heart wall. A set of one or more tensioning members 426 may be routed within the half 422 around the right side of the heart, and an independent set of tensioning members 428 are routed within the half 424 around the left side of the heart. These two sets of tensioning members 426, 428 may be independently cinched to allow selective control of force or constraint on either the mitral annulus (left heart) or tricuspid annulus (right heart).

Figure 19:
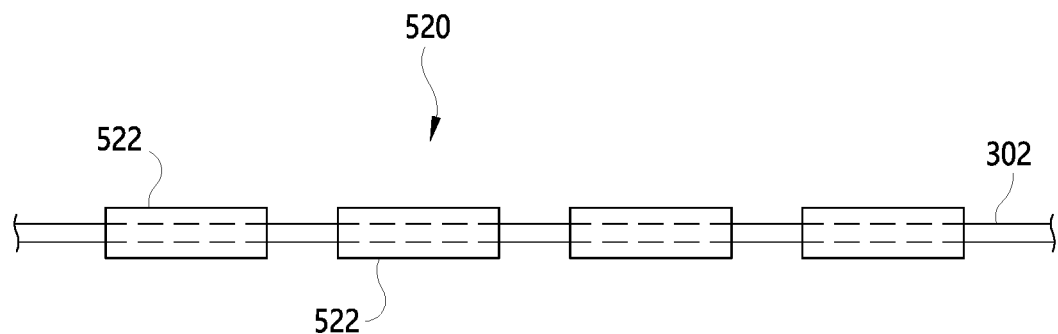
FIG. 19 is a partial side view of an embodiment of a protective member.

In some embodiments, a protective member may be or include an inflatable balloon or bladder that creates constraint as it is inflated against heart tissue. In FIG. 19, a protective member 520 includes a series of independent balloons or bladders 522 joined together (as by sutures or other flexible connections) that form segments or sections of an annuloplasty device enabling localized application of forces or constraint to the heart. A tensioning member and/or protective member as described above may extend through a known radially-expanding balloon, as one example, so that the balloon can inflate at least on the side facing heart tissue. There may be a left-sided balloon or bladder and right-sided balloon or bladder to allow independent control of either side of the heart tissue, as discussed above with respect to protective member 420.

As discussed above with respect to belt 20, protective members in various embodiments may be formed or configured differently (e.g. to be wider) at certain sections of the AV groove, where there is greater risk of coronary occlusion. Likewise, protective members in various embodiments may be heat-set into various shapes, such as a saddle shape to conform to a saddle-shaped AV groove.

A particular example of a protective member 620 (FIGS. 20A-20C) may be or include a flattened, belt-like weave 622 that is heat-set into place. Multiple passages 624 are formed in weave 622, so as to allow passage of multiple (e.g. 2 or 3) tensioning members through protective member 620 and generally parallel to each other. Protective member 620 may be made from nitinol filaments or strips, heat-set over parallel mandrels 626, so that multiple distinct passages are formed. In that illustrated embodiment, the cross-section of protective member 620 has three lumens 624 for three independent tensioning members to pass through. FIG. 20B shows a basic weave with three channels or passages 624, and FIG. 20C shows two side passages 624 with an extra loop. A center passage may be used between the side extra-loop passages.

Figure 21:
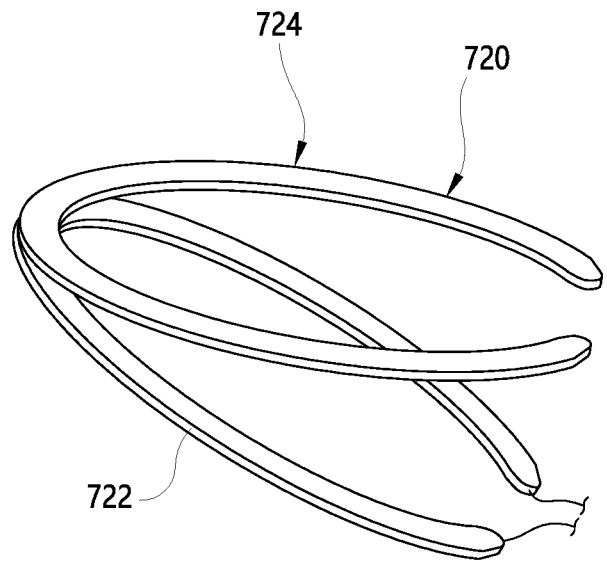
FIG. 21 is a schematic illustration of an embodiment of a protective member.

Embodiments of tensioning members and/or protective members as described herein can also include an auxiliary arm for providing additional tension or constraint to the heart in a location additional to that affected by a main part the tensioning member and/or protective member. In the embodiment shown schematically in FIG. 21, a tensioning member and/or protective member 720 includes such an auxiliary arm 722 joined to the main member 724. Arm 722 can pivot or otherwise be adjusted with respect to main member 724. While main member 724 wraps around the AV groove or other desired location on the heart, arm 722 wraps around another location, such as a lower point on the ventricle. Arm 722 in this embodiment joins with main member 724 near the junction of the right and left hearts when protective member 720 is implanted. In such an embodiment, arm 722 could pass lower on the free wall of the ventricles, thereby applying constraint to the heart at the anchor points of the papillary muscles, and further improving the ability of one or both of the mitral and tricuspid valve leaflets to close properly.

Tensioning members and/or protective members as disclosed herein are intended to provide ease of initial placement and adjustment as they are being implanted. Free ends of tensioning members and/or protective members as disclosed herein can be pulled to tighten around the heart, held temporarily to allow the surgeon to assess placement, amount of tension or other factors, and then can be easily adjusted before permanent locking, or easily removed if withdrawal is indicated.

Tensioning member embodiments preferably include two parallel members or portions (e.g. 304, 306 in FIG. 13 or 80, 82 in FIGS. 8, 9, 11) that connect together or are adjacent at an end. That end can be drawn through a sliding hole or loop at an end of the protective member and/or tensioning member. The hole or loop may be or include any of a number of structures. For example, a tensioning member may include a loop in itself, through which the adjacent or connecting ends pass (akin to a noose knot). The sliding loop in the tensioning member may be held fixedly as the surgeon draws the end through it, resulting in tightening of the tensioning member.

Figure 22:
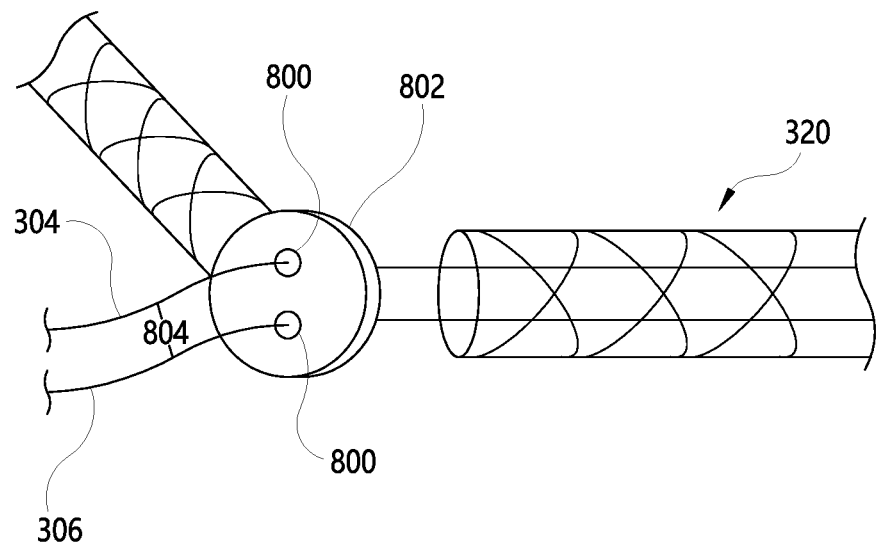
FIG. 22 is a perspective view of ends of an embodiment of a protective member with an embodiment of a locking disc.

In a similar arrangement, the parallel tensioning member portions (e.g. 304, 306) pass independently through respective holes 800 in a button-shaped disc 802 fixed to one end of the tensioning member or protective member (FIG. 22). The surgeon may pull legs 304, 306 through their respective holes 800 to tighten the tensioning member (and any protective member) around the heart. When a sufficient amount of tension has been applied by pulling, the two legs may be held or joined together (i.e. in a knot or joint as at location 804). When the two legs 304, 306 are tied or joined together, the joint at 804 cannot pass through holes 800, thus locking the tensioning member length as desired. As an alternative to a separate disc 802, a pair of parallel loops may be heat-set into the end of a protective member (e.g. a nitinol braid protective member) to provide holes 800 and serve the function of preventing passage of the tied or joined legs 304, 306 and preserving tension.

In that example, the two legs 304, 306 may be temporarily held or joined together with a temporary clamp (e.g. a hemostat) or other locking device to prevent back passage through holes 800. This allows the surgeon to set a level of constraint temporarily, by pulling legs 304, 306 through holes 800, and then assess the physiologic response before permanently locking the tensioning member length.

Figure 23:
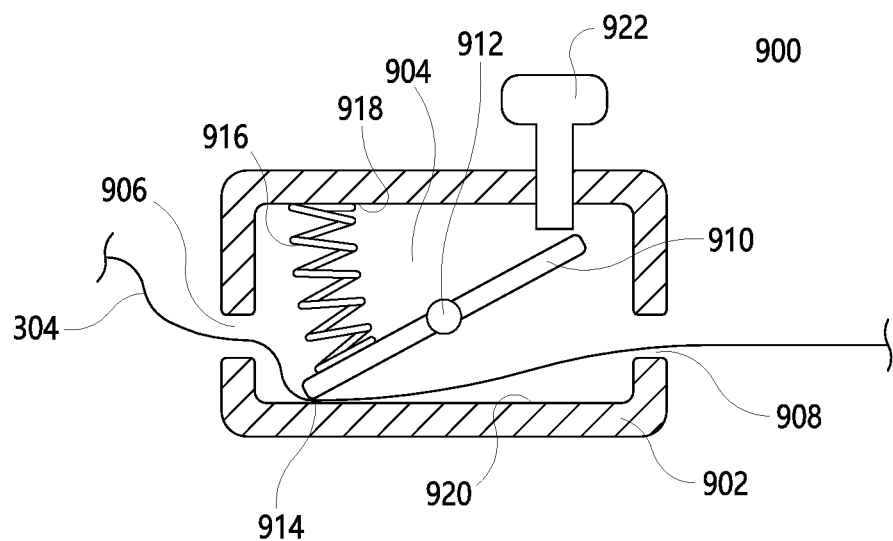
FIG. 23 is a part-cross-sectional view of an embodiment of a locking mechanism.

Other types of locking structures may be fixedly attached to one end of tensioning member(s) (e.g. 302) and/or protective member (e.g. 320). One example of such a locking structure 900 is shown schematically in FIG. 23. Lock 900 includes a body 902 shown in cross-section as a cylinder, so as to minimize edge surfaces on the implantable lock. Body 902 defines a passage or chamber 904 with openings 906, 908, shown in one embodiment to be opposite each other. Within passage 904 is a bar or jaw 910 pivotably anchored to body 902 by an axle or pivot point 912. An engagement end of jaw 910 may include a roughened or toothed portion 914 for engaging suture(s) or other tensioning member(s) passing through passage 904. A spring 916 is fixed to an internal surface 918 of body 902 into passage 904, and contacts a surface of jaw 910 opposite roughened portion 914, so as to bias jaw 910 away from surface 918 and toward or against an opposing surface 920 within passage 904. A button 922 is connected to body 902 so as to be in contact with (or be able to be placed in contact with) a lever end of jaw 910, which is opposite to the jaw's engagement end, to the opposite side of axle or pivot point 912.

One or more adjustable ends (e.g. 304, 306) of one or more tensioning members (e.g. 302) may thread through passage 904 via openings 906, 908. As noted above, locking structure 900 in the illustrated embodiment is normally closed through the bias of spring 916. By pressing button 922 to pivot jaw 910 and move the engagement end away from a surface of passage 904, such suture or tensioning member portion(s) may slide along or in and out of locking structure 900. When button 922 is released, jaw 910 pivots under the bias of spring 916 so that roughened portion 914 presses the suture or tensioning member portion(s) against a surface of passage 904. Locking structure 900 is thus locked, with adjustable end(s) of the tensioning member(s) being fixed within locking structure 900, holding the tensioning member at a particular length and amount of constraint upon the heart. Movement of the tensioning member(s) is restricted until button 922 is pressed to pivot jaw 910 and open the lock, allowing the tensioning member to be slide through the lock 900 and its overall length to be adjusted. Thus, lock 900 may have a temporary locked position, allowing unlocking and further adjustment as needed, but may be left in a permanently locked state as desired. Lock 900 may include a shape or particular exterior surfaces that allow an interface with a holding or gripping tool so as to make manipulation of lock 900 and tensioning member(s) through it easier.

In other embodiments, a locking structure may be normally open, e.g. with jaw 910 biased by a spring (e.g. 916) to an open position allowing sliding passage of the tensioning member(s) until it is actuated by a tool or handle designed to press jaw 910 against the tensioning member(s), or otherwise allow it to engage the tensioning member(s). Such a tool may have clamping jaws (e.g. a hemostat). In some embodiments, multiple jaws 910 may be present that pivot or operate together, like a hemostat, within lock 900. Other types of locking structures may be used, such as those described in application Ser. No. 16/394,192 (filed Apr. 25, 2019) and PCT US2019/032216 (filed May 14, 2019), incorporated herein by reference in their entireties.

Embodiments of the open-surgical system described herein include the ability not only to make adjustments to an annuloplasty implant during placement, but to control, assess, and provide information concerning the tightening of the system and its effects. As discussed above, a tensioning member (with or without a protective member) may be initially placed around the heart, and placed in tension to provide correction to valve problems or other cardiac issues. Tension can be applied in a number of ways, for example by pulling on an adjustable end of a tensioning member while supporting or providing counter-traction to another section of the tensioning member, and/or to a lock structure, sliding loop or disc connected to it (as described above). The adjustable end of the tensioning member might be drawn with a tool, such as a ratcheting pulling tool designed for one-handed operation.

Figure 24:
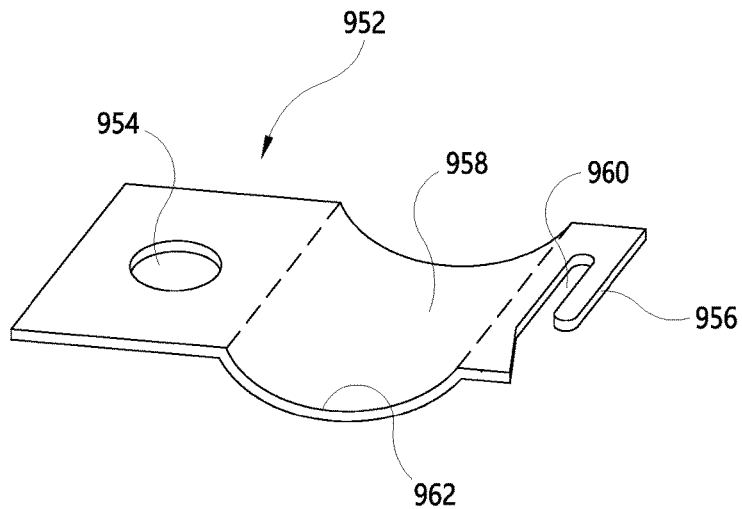
FIG. 24 is a perspective view of an embodiment of a stabilizing plate for holding and/or adjusting a tensioning member and/or protective member in tension.
Figure 25:
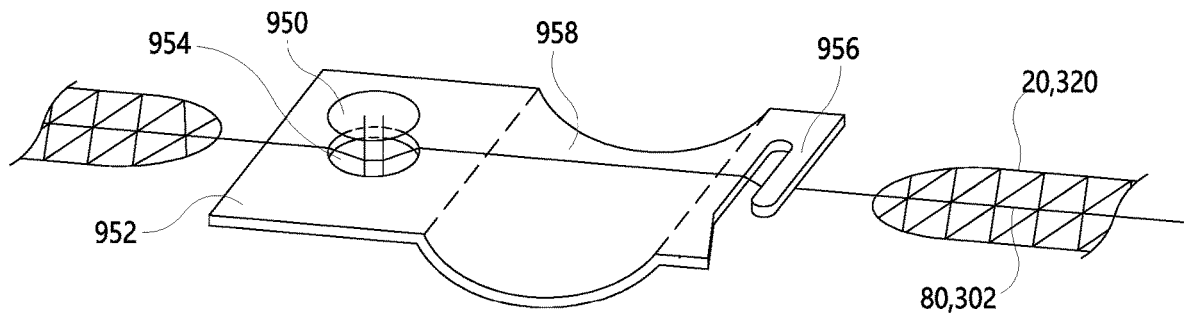
FIG. 25 is a perspective view of the embodiment of a stabilizing plate of FIG. 24 with embodiments of additional structure and a tensioning member and protective member.
Figure 26:
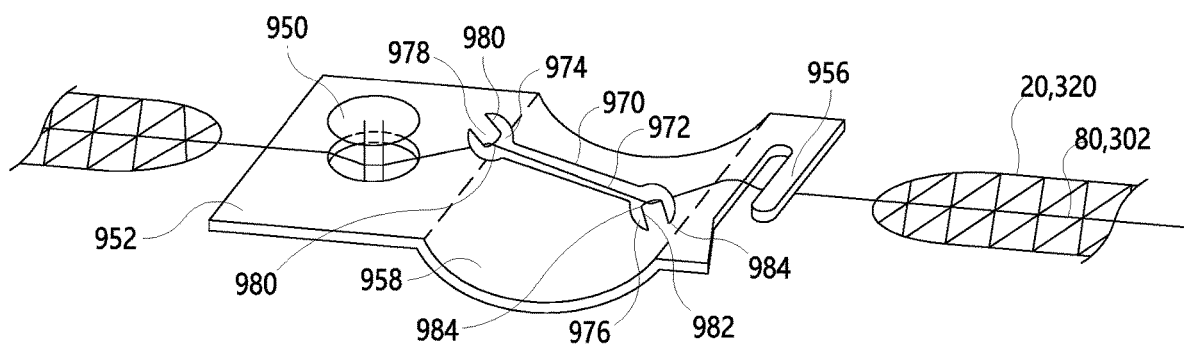
FIG. 26 is a perspective view of the embodiments shown in FIG. 25 along with an embodiment of a guide tool.

An example of structure that can be used to assist in tightening tensioning member(s) and/or protective member (s) is shown in FIGS. 24-26. An example of a suture or tensioning member 302 is shown extending from a protective member or belt (e.g. 20, 320). Each free end 304, 306 of tensioning member 302 is tied to or otherwise fixed to a spool 950. A stabilizing plate 952 is also provided, having a well 954, a stabilizing arm 956, and a valley 958 between arm 956 and well 954. Well 954 has a dimension approximately the same as the greatest outer dimension of a base of spool 950, so that spool 950 can be inserted into well 954. In specific embodiments, spool 950 has a close fit with an inner wall of well 954, so that spool 950 does not rotate with respect to plate 952 after insertion. Arm 956 is separated by slot 960 from the body of plate 952, and in the illustrated embodiment both slot 960 and arm 956 are substantially parallel to valley 958. While well 954 and arm 956 are in portions of plate 952 that are in the same plane in this embodiment, valley 958 joins with those portions but is curved (e.g. cylindrically) out of that plane. Valley 958 has a concave surface 962 that is below (as seen in FIGS. 24-26) the plane of the remainder of plate 952.

A guide tool 970 is also shown, which includes a central shaft or bar 972 and opposed ends 974, 976. Ends 974, 976 are enlarged compared to shaft 972, and may be substantially circular with a diameter about twice the width of shaft 972. End 974 includes a gap or slot 978 which is rectangular in the illustrated embodiment, having side surfaces 980 that are substantially parallel to a longitudinal axis of shaft 972. End 976 includes a gap or slot 982 which is also rectangular in the illustrated embodiment, but with side surfaces 984 that are oblique (e.g. about 30 to 45 degrees) with respect to a longitudinal axis of shaft 972.

In an example of use, protective member 20, 320 is mechanically positioned (e.g. in an open surgical procedure) around the heart, with slack in tensioning member 302 accommodating variability of size and ease of positioning. Spool 950 (with attached ends of tensioning member 302) is placed in well 954 of stabilizing plate 952, with tensioning member entering slot 960 to run between arm 956 and the rest of plate 952 and over valley 958. The surgeon can then pre-tension the protective member and tensioning member by gathering slack in the tensioning member into one or more loops that are place around spool 950. Alternatively, if there is excess slack in the tensioning member, a portion of the tensioning member can be removed, and the tensioning member can be re-tied or otherwise reconnected to spool 950. Valley 958 makes manipulation of the tensioning member easier (whether by hand or by tool) by maintaining a space between plate 952 and the tensioning member. Valley 958 thus allows a finger or tool to be easily maneuvered under the tensioning member so that it can be gripped.

Guide tool 970 is placed so that end 974 generally faces spool 950, shaft 972 crosses valley 958, and end 976 is adjacent arm 956. Gap 982 faces away from arm 956. Guide tool 970 is also placed so that tensioning member 302 runs through or around gaps 978, 982 as it goes from slot 960 to spool 950. The surgeon can then fine-tune tension in the tensioning member by winding (to tighten) or unwinding (to loosen) the tensioning member around spool 950. Guide tool 970 ensures that the tensioning member remains in place and untwisted as the tensioning member is wound or unwound from the spool. When the desired tension has been achieved, guide tool 970 may be removed. Spool 950, plate 952 and/or tool 970 may be made of biocompatible materials, and at least spool 950 and plate 952 may remain in the body after the procedure is completed.

Other devices for drawing slack and pulling and adjustable end of a tensioning member to tighten the tensioning member (and/or protective member) around a heart are contemplated. For example, a spool 1000 may be rotatably mounted to an end of the protective or tensioning members, with an adjustable end of tensioning member(s) fixed to or loopable around the spool. As the spool is rotated (e.g. using a gripping or rotating tool directly, or remotely through the use of a long flexible torque coil), the adjustable end of tensioning member(s) are drawn around the spool to take up slack and/or tighten it. Such a spool allows better mechanical isolation of the heart tissue from the application of forces.

Figure 27:
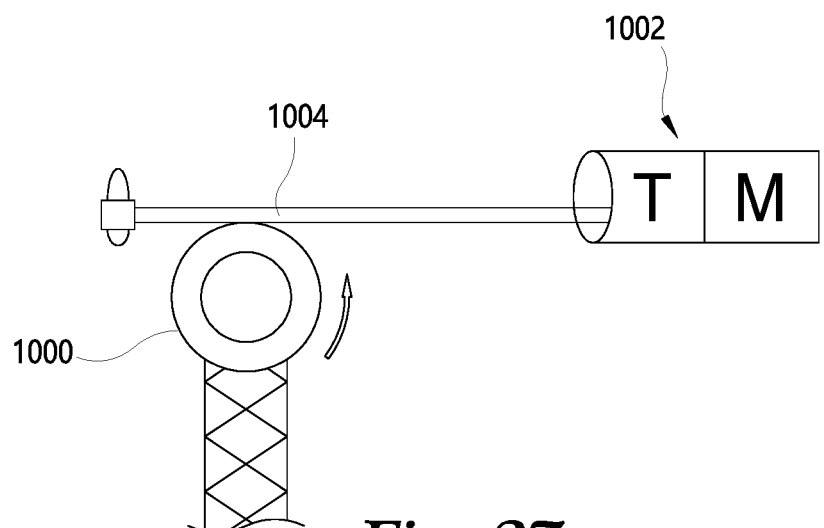
FIG. 27 is a schematic illustration of an embodiment of a mechanism for tightening and/or adjusting tension on a tensioning member and/or a protective member.
Figure 28:
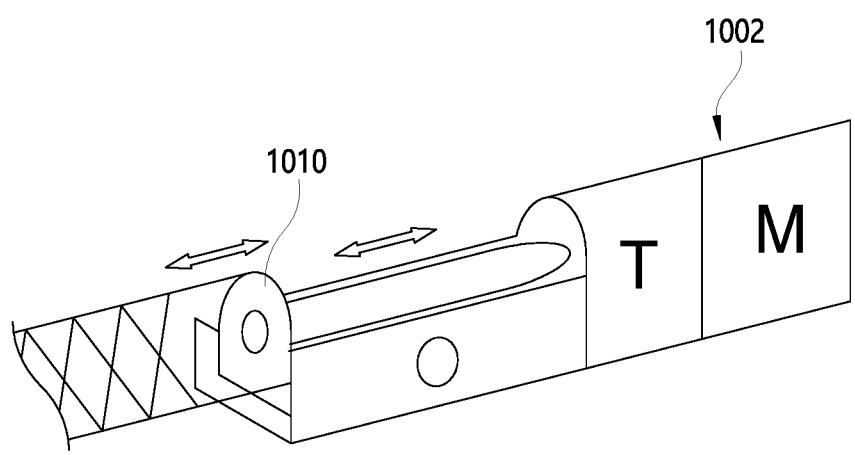
FIG. 28 is a schematic illustration of an embodiment of a mechanism for tightening and/or adjusting tension on a tensioning member and/or a protective member.

An implantable miniature motor and/or transmission 1002 may be used with spool 1000 or with other structure in order to tighten tensioning member(s). As seen schematically in FIG. 27, motor and/or transmission 1002 may turn a drive shaft 1004 (e.g. forming a worm-gear drive) that is connected to spool 1000, turning spool 1000 (as indicated by the arrow) to draw slack in tensioning member(s). In particular embodiments, the motor and/or transmission 1002 is remotely controllable. In this way, adjustability of the tension of tensioning member(s) (and therefore force on the heart) can be maintained even after the implantation is completed and the surgical site closed. Alternatively, in place of a spool, an implanted linear slide 1010 (FIG.) may be connected to the adjustable end of tensioning member(s), and also to a motor and/or transmission 1002. Whether motor and/or transmission 1002 rotates or moves linearly shaft 1004, slide 1010 moves toward motor and/or transmission 1002 to draw the slack of the tensioning member(s) and increase tension.

Devices and methods for measuring the amount (length) of tensioning member(s) and/or protective member(s) that have been drawn for tightening are also contemplated. For example, in embodiments noted above having a motor 1002, the motor mechanism can include an encoder that measures the displacement of the tensioning member(s). That amount of displacement can be monitored or used to calculate the amount of constriction applied to the heart. The motor mechanism may also or alternatively allow the user to indirectly measure the tension load based on the current draw on the motor. As the current draw increases with increased tension, the two factors can be correlated to provide an estimate of tension on the tensioning member(s).

As other examples, embodiments as described herein can include one or more torque sensors attached to a motor shaft or to a spool used to take up the tensioning member(s), to measure applied tension. A load cell may be placed in series with a tensioning member to measure tension applied to it, or a tensioning member may be run over a pulley or spool attached to a load cell to measure applied tension. Tensioning member(s) or protective member(s) may be marked in increments (e.g. in millimeters or tenths of millimeters) to allow the surgeon to directly observe the amount of displacement during tightening. Similarly, a tensioning member may be tightened using a pulling or other tensioning tool that has a scale or gauge for measuring displacement or tension.

As tightening is taking place, information or instructions relating to the tension on and/or displacement of tensioning member(s) can be sent to or received from a remote monitor or controller. For example, the signals from a tension sensor or displacement sensor as described above may be transmitted wirelessly, optically, acoustically or via wires to a computer, viewscreen or other external monitor or controller. An implantable monitor or controller may also collect, store and apply control signals to a motor (as described above) as desired, and in particular embodiments can include a transmitter to send collected data (e.g. concerning tension, heart function, or other variables) periodically to a remote monitor for access by a clinician. Such a controller and/or monitor system allows periodic monitoring of the annuloplasty system without invasive procedures. The system may include a control loop allowing tightening or loosening the tensioning member (e.g. via an implanted motor) depending on the observed tension. The system may notify or alarm the patient and/or clinician if changes are made to tension, or if changes in observed tension are noted.

Other examples of sensors that can be included with an annuloplasty device as described herein are accelerometers mounted to tensioning member(s) and/or protective member(s), or a microphone attached to or associated with them. An accelerometer could detect cardiac motion and be used as a surrogate for direct measure of stroke volume or ejection fraction. This information could either allow directed adjustment of the device tension, or it could be used as diagnostic information for heart failure management of the patient through pharmacologic or other means. A microphone can be focused at the valves (mitral and/or tricuspid) and be used to assess regurgitation. The signal could be used to direct further adjustments to the annuloplasty device as needed to minimize regurgitation.

In some embodiments, an annuloplasty device as described herein (tensioning member(s) and/or protective member(s)) may include electrodes contacting the right atrium, right ventricle, left atrium, and/or left ventricle. Such electrodes sense and provide electrogram timing information from each of the chamber(s), and can be used to pace the chamber(s). Larger electrodes (or a single large electrode) may be incorporated into the device for defibrillation. Electrodes may also be used to sense impedance changes associated with volume changes during the cardiac cycle or impedance changes associated with fluid overload as a result of heart failure. Independent adjustment of the right and left sides of the heart may allow control of fluid distribution through the heart and body and can be directed based on information sensed by the electrodes. Satellite electrodes may be placed, connected to the annuloplasty device via wire tethers if pacing and sensing locations separate from the AV groove region are desired. Further, a pulse generator may be incorporated into the annuloplasty device, allowing pacing without transvenous leads placed within the heart or crossing heart valves.

In the discussion above, particular attention was drawn to the use of the devices described herein in an open-surgical annuloplasty procedure, i.e. by placing a constricting tensioning member(s) and/or protective member(s) around the heart in a direct manner. It will be understood that structures, steps and features described above may be used in connection with other bodily structures, therapies or surgical procedures.

While the disclosure has been illustrated and described in detail in the drawings and foregoing description, the same is to be considered as illustrative and not restrictive in character, it being understood that only selected embodiments have been shown and described and that all equivalents, changes, and modifications that come within the spirit of the disclosures as defined herein or by the following claims are desired to be protected. It will be understood that features described particularly with respect to one or more specific structures or embodiments may be incorporated into or otherwise used with other structures or embodiments as disclosed herein.

The following numbered clauses set out specific embodiments that may be useful in understanding the present invention:

1. A belt for placement along the atrioventricular groove of the heart, comprising:
    a mesh tube having a first open end and a second open end and a lumen passing through the tube from the first open end to the second open end along a longitudinal axis of the tube, the tube configured longitudinally in a loop so as to be placed around the heart and along the atrioventricular groove;

a first suture portion within the tube, the first suture portion fixed to the tube adjacent the first open end and extending through the lumen toward the second open end, the first suture portion connected to the tube within the lumen by a plurality of holding elements so that the first suture portion is longitudinally movable through the holding elements with respect to the tube;

a second suture portion within the tube and parallel to and spaced from the first suture portion, the second suture portion fixed to the tube adjacent the first open end and extending through the lumen toward the second open end, the second suture portion connected to the tube within the lumen by a plurality of holding elements so that the second suture portion is longitudinally movable through the holding elements with respect to the tube;

wherein pulling the first and second suture portions cinches the tube to reduce an area of the loop so that the tube compress longitudinally in at least selected locations along the tube.

2. The belt of clause 1, wherein the first suture portion and second suture portion each extend through the second open end of the tube to provide respective parts of the first and second suture portions that are outside the tube and able to be pulled to cinch the tube.

3. The belt of any of clauses 1-2, wherein the first suture portion and second suture portion are parts of a single tensioning suture, having a middle portion between the first suture portion and second suture portion, and further comprising a locking suture attached to the middle portion of the tensioning suture.

4. The belt of any of clauses 1-3, further comprising a ring within the tube and adjacent the second open end, wherein the tensioning suture folds over and through the ring, wherein the first and second suture portions are on one side of the ring and the middle portion is on the other side of the ring.

5. The belt of clause 4, wherein the ring includes a rounded engagement portion around which the tensioning suture is folded.

6. The belt of clause 4, wherein the ring includes first and second linear sides that parallel the tube adjacent the second open end, the first linear side connected to the tube by at least one holding element, and the second linear side connected to the tube by at least one holding element.

7. The belt of any of clauses 3-6, wherein the locking suture includes a plurality of protrusions for use in holding tension applied to the locking suture and transmitted to the first and second suture portions.

8. The belt of clause 7, wherein the locking suture has a length within the tube and a portion exiting the tube through the first open end, and wherein the protrusions are on up to the full length of the locking suture within the tube and next to the first open end, and are not otherwise on the length of the locking suture within the tube.

9. The belt of any of clauses 1-8, wherein the mesh is nitinol.

10. The belt of any of clauses 1-9, wherein the mesh is heat-set so that when the tube reaches body temperature, its cross section assumes a barbell shape.

11. The belt of any of clauses 1-9, wherein the mesh is heat-set so that when the tube reaches body temperature, its cross section assumes an elliptical or oval shape.

12. The belt of any of clauses 1-9, wherein the mesh is heat-set so that when the tube reaches body temperature, it assumes a flat ribbon shape.

13. The belt of any of clauses 1-9, wherein the mesh is heat-set so that when the tube reaches body temperature, it assumes a shape with a first region having a first hoop diameter and first cross sectional dimension, and a second region having a second hoop diameter and second cross sectional dimension, and wherein the first hoop diameter is greater than the second hoop diameter, and the first cross sectional dimension is greater than the second cross sectional dimension.

14. The belt of clause 13, wherein a medial portion between the first and second regions includes a contour adapted to conform to at least part of the atrioventricular groove.

15. The belt of any of clauses 1-9, wherein the mesh is heat-set so that when the tube reaches body temperature, it assumes a saddle shape having one or more lower rounded contoured regions, and wherein at least one of the lower rounded contoured regions is adapted to fit closely within the atrioventricular groove.

16. The belt of any of clauses 1-15, wherein the two suture portions are each part of a respective separate suture.

17. The belt of any of clauses 1-16, wherein the two suture portions are connected to form a loop.

18. The belt of clause 17, wherein the loop is connected to an elongated element at least partially exterior to the belt, the elongated element being one of a locking suture and a delivery filament.

19. An annuloplasty system for use in open-surgical procedures, comprising:
a tensioning member adapted to be implanted by wrapping around the heart outside of a catheter system;
locking means for holding the tensioning member in tension around the heart and for permitting adjustment of tension in the tensioning member.

20. The annuloplasty system of clause 19, further comprising a protective member through which the tensioning member passes, the protective member having guides for the tensioning member and being of a shape-memory material that resists twisting.

21. The annuloplasty system of clause 20, wherein the protective member has a first ring half adapted for attachment to a first portion of the heart and a second portion adapted for attachment to a second portion of the heart.

22. The annuloplasty system of clause 20, wherein the tensioning member includes first and second legs, and the locking means is attached to the protective member and includes first and second holes, wherein the first leg extends through the first hole and the second leg extends through the second hole, and the legs may be held at a holding location, wherein the first and second holes are situated between the holding location and the protective member.

23. The annuloplasty system of clause 20, wherein the locking means includes a stabilizing plate having a well and a valley section, and a spool seated in the well, wherein the tensioning member may be wrapped around the spool to increase tension on the tensioning member and unwrapped from the spool to reduce tension on the tensioning member.

24. The annuloplasty system of clause 20, further comprising at least one of a miniature motor and transmission operatively connected to the tensioning member, wherein operation of the at least one of a miniature motor and transmission is adapted to perform at least one of tightening and loosening the tensioning member when the tensioning member is placed around the heart.

25. The annuloplasty system of clause 19, further comprising a device operatively connected to the tensioning member for directly or indirectly measuring tension or length of the tensioning member that has been displaced in tightening the tension member, the device from the group consisting of an encoder to measure displacement of the tensioning member; a sensor measuring current draw on a motor operatively connected to the tensioning member; a torque sensor operatively connected to the tensioning member; a load cell placed in series with the tensioning member; a tensioning tool including a scale or gauge for measuring displacement of the tensioning member.

What is claimed is:

1. An annuloplasty system for use in open-surgical procedures, comprising:
    a tensioning member adapted to be implanted by wrapping around the heart, wherein said tensioning member comprises an elongate member forming a continuous loop configured to be positioned around the heart;
    a protective member through which the tensioning member passes, the protective member being of a shape-memory material that resists twisting such that a widened dimension of the protective member contacts with the heart, the protective member comprising a material visible with one or more of the following: fluoroscopy, CT scanning, ultrasound imaging, and/or magnetic resonance imaging, and wherein the protective member comprises a continuous ring structure;
    locking means for holding the tensioning member in tension around the heart and for permitting adjustment of tension in the tensioning member.

2. The annuloplasty system of claim 1, the protective member having guides for the tensioning member.

3. The annuloplasty system of claim 2, wherein the locking means includes a stabilizing plate having a well and a valley section, and a spool seated in the well, wherein the tensioning member may be wrapped around the spool to increase tension on the tensioning member and unwrapped from the spool to reduce tension on the tensioning member.

4. The annuloplasty system of claim 2, further comprising at least one of a miniature motor and transmission operatively connected to the tensioning member, wherein operation of the at least one of a miniature motor and transmission is adapted to perform at least one of tightening and loosening the tensioning member when the tensioning member is placed around the heart.

5. The annuloplasty system of claim 1, further comprising a device operatively connected to the tensioning member for directly or indirectly measuring tension or length of the tensioning member that has been displaced in tightening the tension member, the device from the group consisting of an encoder to measure displacement of the tensioning member; a sensor measuring current draw on a motor operatively connected to the tensioning member; a torque sensor operatively connected to the tensioning member; a load cell placed in series with the tensioning member; a tensioning tool including a scale or gauge for measuring displacement of the tensioning member.

6. The annuloplasty system of claim 1, wherein said locking means comprises a first buckle configured to engage the tensioning member at a first location.

7. The annuloplasty system of claim 6, wherein said locking means comprises a second buckle configured to engage the tensioning member at a second location.

8. The annuloplasty system for use in open-surgical procedures, comprising:
    a tensioning member adapted to be implanted by wrapping around the heart, wherein said tensioning member comprises an elongate member forming a loop configured to be positioned around the heart;
    locking means for holding the tensioning member in tension around the heart and for permitting adjustment of tension in the tensioning member, wherein said locking means comprises a first buckle configured to engage the tensioning member at a first location, wherein said locking means comprises a second buckle configured to engage the tensioning member at a second location, and wherein said tensioning member comprises an elongate member forming a loop having a first end attached to said first buckle and a second end attached to said second buckle;
    a first portion of said tensioning member slideably received in said second buckle, the first portion being towards the first end of the tensioning member; and
    a second portion of said tensioning member slideably received in said first buckle, the second portion being towards the second end of the tensioning member, such that as the first buckle and the second buckle are pushed apart the tensioning member is tightened.

9. The annuloplasty system of claim 8, further comprising a protective member through which the tensioning member passes, the protective member having guides for the tensioning member and being of a shape-memory material that resists twisting.

10. An annuloplasty system for use in open-surgical procedures, comprising:
    a tensioning member adapted to be implanted by wrapping around the heart, wherein said tensioning member comprises an elongate member forming a continuous loop configured to be positioned around the heart;
    a protective member through which the tensioning member passes, the protective member being of a shape-memory material that resists twisting such that a widened dimension of the protective member contacts with the heart, the protective member comprising a material visible with one or more of the following: fluoroscopy, CT scanning, ultrasound imaging, and/or magnetic resonance imaging;
    locking means for holding the tensioning member in tension around the heart and for permitting adjustment of tension in the tensioning member, wherein said locking means comprises a first buckle configured to engage the tensioning member at a first location.

11. The annuloplasty system of claim 10, wherein said locking means comprises a second buckle configured to engage the tensioning member at a second location.

* * * * *